US008617152B2

(12) United States Patent  
Werneth et al.

(10) Patent No.: US 8,617,152 B2
(45) Date of Patent: Dec. 31, 2013

(54) ABLATION SYSTEM WITH FEEDBACK

(75) Inventors: Randell L. Werneth, San Diego, CA (US); Marshall L. Sherman, Cardiff-by-the-Sea, CA (US); J. Christopher Flaherty, Topsfield, MA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1861 days.

(21) Appl. No.: 11/179,332

(22) Filed: Jul. 12, 2005

(65) Prior Publication Data

US 2006/0106375 A1    May 18, 2006

Related U.S. Application Data

(60) Provisional application No. 60/628,090, filed on Nov. 15, 2004.

(51) Int. Cl.
*A61B 18/18* (2006.01)
(52) U.S. Cl.
USPC ............... 606/32; 606/33; 606/41; 606/45
(58) Field of Classification Search
USPC ............... 606/32–41; 607/122; 600/439
See application file for complete search history.

(56) References Cited

U.S. PATENT DOCUMENTS

| 3,516,412 | A |   | 6/1970  | Ackerman |
|-----------|---|---|---------|----------|
| 3,951,136 | A |   | 4/1976  | Wall ......................... 128/2.06 E |
| 4,017,903 | A |   | 4/1977  | Chu |
| 4,112,952 | A |   | 9/1978  | Thomas et al. |
| 4,409,986 | A | * | 10/1983 | Apple et al. ................... 600/528 |
| 4,411,266 | A |   | 10/1983 | Cosman |
| 4,432,377 | A |   | 2/1984  | Dickhudt |
| 4,660,571 | A |   | 4/1987  | Hess et al. |
| 4,699,147 | A |   | 10/1987 | Chilson et al. |
| 4,785,815 | A |   | 11/1988 | Cohen |
| 4,860,769 | A |   | 8/1989  | Fogarty et al. |
| 4,869,248 | A |   | 9/1989  | Narula |
| 4,882,777 | A |   | 11/1989 | Narula |
| 4,896,671 | A |   | 1/1990  | Cunningham et al. |
| 4,907,589 | A |   | 3/1990  | Cosman |

(Continued)

FOREIGN PATENT DOCUMENTS

| AU | 5200671 | 10/2005 |
|----|---------|---------|
| CA | 2327322 | 11/1999 |

(Continued)

OTHER PUBLICATIONS

Kunis et al.; U.S. Appl. No. 12/197,425 entitled "Atrial ablation catheter and method of use,", filed Aug. 25, 2008.

(Continued)

*Primary Examiner* — Linda Dvorak
*Assistant Examiner* — Amanda Scott
(74) *Attorney, Agent, or Firm* — Christopher & Weisberg, P.A.

(57) ABSTRACT

Devices, systems and methods are disclosed for the ablation of tissue and treatment of cardiac arrhythmia. An ablation system includes an ablation catheter that has an array of ablation elements and a location element, an esophageal probe also including a location element, and an interface unit that provides energy to the ablation catheter. The distance between the location elements, determined by calculating means of the system, can be used by the system to set or modify one or more system parameters.

42 Claims, 6 Drawing Sheets

(56) References Cited

U.S. PATENT DOCUMENTS

| | | | |
|---|---|---|---|
| 4,920,980 A | 5/1990 | Jackowski | |
| 4,940,064 A | 7/1990 | Desai | |
| 4,966,597 A | 10/1990 | Cosman | |
| 5,010,894 A | 4/1991 | Edhag | 128/785 |
| 5,016,808 A | 5/1991 | Heil, Jr. et al. | |
| 5,083,565 A | 1/1992 | Parins | |
| 5,100,423 A | 3/1992 | Fearnot | |
| 5,156,151 A | 10/1992 | Imran | |
| 5,184,621 A | 2/1993 | Vogel et al. | |
| 5,199,433 A * | 4/1993 | Metzger et al. | 600/380 |
| 5,215,103 A | 6/1993 | Desai | |
| 5,228,442 A | 7/1993 | Imran | |
| 5,230,349 A | 7/1993 | Langberg | |
| 5,231,987 A | 8/1993 | Robson | |
| 5,231,995 A | 8/1993 | Desai | |
| 5,234,004 A | 8/1993 | Hascoet et al. | |
| 5,239,999 A | 8/1993 | Imran | |
| 5,255,679 A | 10/1993 | Imran | |
| 5,279,299 A | 1/1994 | Imran | |
| 5,281,213 A | 1/1994 | Milder et al. | |
| 5,281,218 A | 1/1994 | Imran | |
| 5,309,910 A | 5/1994 | Edwards et al. | |
| 5,313,943 A | 5/1994 | Houser et al. | |
| 5,318,525 A | 6/1994 | West et al. | |
| 5,324,284 A * | 6/1994 | Imran | 606/15 |
| 5,327,889 A | 7/1994 | Imran | |
| 5,330,466 A | 7/1994 | Imran | |
| 5,334,193 A | 8/1994 | Nardella | |
| 5,342,295 A | 8/1994 | Imran | |
| 5,342,357 A | 8/1994 | Nardella | |
| 5,345,936 A | 9/1994 | Pomeranz et al. | |
| 5,348,554 A | 9/1994 | Imran et al. | |
| D351,652 S | 10/1994 | Thompson et al. | |
| 5,364,352 A | 11/1994 | Cimino et al. | |
| 5,365,926 A | 11/1994 | Desai | |
| 5,370,644 A | 12/1994 | Langberg | |
| 5,370,675 A * | 12/1994 | Edwards et al. | 607/101 |
| 5,383,917 A | 1/1995 | Desai | |
| 5,391,147 A | 2/1995 | Imran et al. | |
| 5,397,304 A | 3/1995 | Truckai | |
| 5,397,339 A | 3/1995 | Desai | |
| 5,400,783 A | 3/1995 | Pomeranz et al. | |
| 5,404,638 A | 4/1995 | Imran | |
| 5,406,946 A | 4/1995 | Imran | |
| 5,411,025 A | 5/1995 | Webster, Jr. | |
| 5,423,808 A | 6/1995 | Edwards et al. | |
| 5,423,811 A | 6/1995 | Imran et al. | |
| 5,433,198 A | 7/1995 | Desai | |
| 5,433,739 A | 7/1995 | Sluijter et al. | |
| 5,443,489 A * | 8/1995 | Ben-Haim | 607/115 |
| 5,445,148 A | 8/1995 | Jaraczewski et al. | |
| 5,462,521 A | 10/1995 | Brucker et al. | |
| 5,462,545 A | 10/1995 | Wang et al. | |
| 5,465,717 A | 11/1995 | Imran et al. | |
| 5,471,982 A | 12/1995 | Edwards et al. | |
| 5,487,757 A | 1/1996 | Truckai et al. | |
| 5,492,119 A | 2/1996 | Abrams | |
| 5,500,011 A | 3/1996 | Desai | |
| 5,507,802 A | 4/1996 | Imran | |
| 5,509,411 A | 4/1996 | Littmann et al. | |
| 5,527,279 A | 6/1996 | Imran | |
| 5,533,967 A | 7/1996 | Imran | |
| 5,536,267 A | 7/1996 | Edwards et al. | |
| 5,540,681 A | 7/1996 | Strul et al. | |
| 5,545,161 A | 8/1996 | Imran | |
| 5,545,193 A | 8/1996 | Fleischman et al. | |
| 5,545,200 A | 8/1996 | West et al. | |
| 5,558,073 A | 9/1996 | Pomeranz et al. | |
| 5,573,533 A | 11/1996 | Strul | |
| 5,575,766 A | 11/1996 | Swartz et al. | |
| 5,575,810 A | 11/1996 | Swanson et al. | |
| 5,578,007 A | 11/1996 | Imran | |
| 5,582,609 A | 12/1996 | Swanson et al. | |
| 5,584,830 A | 12/1996 | Ladd et al. | |
| 5,588,432 A | 12/1996 | Crowley | |
| 5,588,964 A | 12/1996 | Imran et al. | |
| 5,595,183 A | 1/1997 | Swanson et al. | |
| 5,596,995 A | 1/1997 | Sherman et al. | |
| 5,598,848 A | 2/1997 | Swanson et al. | |
| 5,601,088 A | 2/1997 | Swanson et al. | |
| 5,606,974 A | 3/1997 | Castellano et al. | |
| 5,607,462 A | 3/1997 | Imran | |
| 5,620,481 A | 4/1997 | Desai | |
| 5,626,136 A | 5/1997 | Webster | |
| 5,630,425 A | 5/1997 | Panescu et al. | |
| 5,630,837 A | 5/1997 | Crowley | |
| 5,637,090 A | 6/1997 | McGee et al. | |
| D381,076 S | 7/1997 | Thornton et al. | |
| 5,645,064 A | 7/1997 | Littmann et al. | |
| 5,645,082 A | 7/1997 | Sung et al. | |
| 5,656,029 A | 8/1997 | Imran et al. | |
| 5,657,755 A | 8/1997 | Desai | |
| 5,658,278 A | 8/1997 | Imran et al. | |
| 5,662,606 A | 9/1997 | Cimino et al. | |
| 5,666,970 A | 9/1997 | Smith | |
| 5,673,695 A | 10/1997 | McGee et al. | |
| 5,680,860 A | 10/1997 | Imran | |
| 5,681,280 A | 10/1997 | Rusk et al. | |
| 5,682,885 A | 11/1997 | Littmann et al. | |
| 5,685,322 A | 11/1997 | Sung et al. | |
| 5,687,723 A | 11/1997 | Avitall | |
| 5,693,078 A | 12/1997 | Desai | |
| 5,697,927 A | 12/1997 | Imran et al. | |
| 5,697,928 A | 12/1997 | Walcott et al. | |
| 5,699,796 A | 12/1997 | Littmann et al. | |
| 5,702,438 A | 12/1997 | Avitall | |
| 5,704,791 A | 1/1998 | Gillio | |
| 5,706,809 A | 1/1998 | Littmann et al. | |
| 5,711,298 A | 1/1998 | Littmann et al. | |
| 5,716,389 A | 2/1998 | Walinsky et al. | |
| 5,722,401 A | 3/1998 | Pietroski et al. | |
| 5,722,975 A | 3/1998 | Edwards et al. | |
| 5,724,985 A | 3/1998 | Snell et al. | |
| 5,733,323 A | 3/1998 | Buck et al. | |
| 5,735,280 A | 4/1998 | Sherman et al. | |
| 5,741,320 A | 4/1998 | Thornton et al. | |
| 5,766,152 A | 6/1998 | Morley et al. | |
| 5,769,791 A | 6/1998 | Benaron et al. | |
| 5,769,847 A | 6/1998 | Panescu et al. | |
| 5,772,590 A | 6/1998 | Webster | |
| 5,775,327 A | 7/1998 | Randolph et al. | |
| 5,782,239 A | 7/1998 | Webster | |
| 5,782,760 A | 7/1998 | Schaer | |
| 5,782,828 A | 7/1998 | Chen et al. | |
| 5,782,899 A | 7/1998 | Imran | |
| 5,792,140 A | 8/1998 | Tu et al. | |
| 5,800,482 A | 9/1998 | Pomeranz et al. | |
| 5,810,740 A | 9/1998 | Paisner | |
| 5,820,568 A | 10/1998 | Willis | |
| 5,827,272 A | 10/1998 | Breining et al. | |
| 5,837,001 A | 11/1998 | Mackey | |
| 5,849,028 A | 12/1998 | Chen | |
| 5,857,464 A | 1/1999 | Desai | |
| 5,857,997 A | 1/1999 | Cimino et al. | |
| 5,860,920 A | 1/1999 | McGee et al. | |
| 5,863,291 A | 1/1999 | Schaer | |
| 5,871,523 A | 2/1999 | Fleischman et al. | |
| 5,873,865 A | 2/1999 | Horzewski et al. | |
| 5,876,399 A | 3/1999 | Chia et al. | |
| 5,881,732 A | 3/1999 | Sung et al. | |
| 5,882,333 A | 3/1999 | Schaer et al. | |
| 5,885,278 A | 3/1999 | Fleischman | |
| 5,891,027 A | 4/1999 | Tu et al. | |
| 5,891,135 A | 4/1999 | Jackson et al. | |
| 5,891,137 A | 4/1999 | Chia et al. | |
| 5,891,138 A | 4/1999 | Tu et al. | |
| 5,893,847 A | 4/1999 | Kordis | |
| 5,893,884 A | 4/1999 | Tu | |
| 5,893,885 A | 4/1999 | Webster | |
| 5,895,355 A | 4/1999 | Schaer | |
| 5,895,417 A | 4/1999 | Pomeranz et al. | |
| 5,897,554 A | 4/1999 | Chia et al. | |
| 5,904,680 A | 5/1999 | Kordis et al. | |
| 5,906,605 A | 5/1999 | Coxum | |

(56) References Cited

U.S. PATENT DOCUMENTS

| | | |
|---|---|---|
| 5,910,129 A | 6/1999 | Koblish et al. |
| 5,911,720 A | 6/1999 | Bourne et al. ............... 606/41 |
| 5,913,854 A | 6/1999 | Maguire et al. |
| 5,916,214 A | 6/1999 | Cosio et al. |
| 5,928,191 A | 7/1999 | Houser et al. |
| 5,931,835 A | 8/1999 | Mackey |
| 5,935,063 A | 8/1999 | Nguyen |
| 5,938,694 A | 8/1999 | Jaraczewski et al. |
| 5,941,845 A | 8/1999 | Tu et al. |
| 5,951,471 A | 9/1999 | de la Rama et al. |
| 5,954,719 A | 9/1999 | Chen et al. |
| 5,957,842 A | 9/1999 | Littmann et al. |
| 5,960,796 A | 10/1999 | Sung et al. |
| 5,967,978 A | 10/1999 | Littmann et al. |
| 5,968,040 A | 10/1999 | Swanson et al. |
| 5,971,980 A | 10/1999 | Sherman |
| 5,992,418 A | 11/1999 | de la Rama et al. |
| 5,997,532 A | 12/1999 | McLaughlin et al. |
| 6,001,093 A | 12/1999 | Swanson et al. |
| 6,001,095 A | 12/1999 | de la Rama et al. |
| 6,002,956 A | 12/1999 | Schaer |
| 6,004,269 A | 12/1999 | Crowley et al. ............... 600/439 |
| 6,014,581 A | 1/2000 | Whayne et al. |
| 6,021,340 A | 2/2000 | Randolph et al. |
| 6,023,638 A | 2/2000 | Swanson |
| 6,029,091 A | 2/2000 | de la Rama et al. |
| 6,032,674 A | 3/2000 | Eggers et al. |
| 6,033,403 A | 3/2000 | Tu et al. |
| 6,042,580 A | 3/2000 | Simpson |
| 6,045,550 A | 4/2000 | Sherman |
| 6,048,329 A | 4/2000 | Thompson et al. |
| 6,049,737 A | 4/2000 | Sherman |
| 6,050,994 A | 4/2000 | Sherman |
| 6,052,612 A | 4/2000 | Desai |
| 6,053,937 A | 4/2000 | Edwards et al. ............... 607/104 |
| 6,056,744 A | 5/2000 | Edwards |
| 6,059,778 A | 5/2000 | Sherman |
| 6,063,077 A | 5/2000 | Schaer |
| 6,063,082 A | 5/2000 | DeVore et al. ............... 606/45 |
| 6,064,902 A | 5/2000 | Haissaguerre et al. |
| 6,068,629 A | 5/2000 | Haissaguerre et al. |
| 6,070,094 A | 5/2000 | Swanson et al. |
| 6,071,274 A | 6/2000 | Thompson et al. |
| 6,071,279 A | 6/2000 | Whayne et al. |
| 6,071,281 A | 6/2000 | Burnside et al. |
| 6,071,282 A | 6/2000 | Fleischman |
| 6,074,351 A | 6/2000 | Houser et al. |
| 6,086,581 A | 7/2000 | Reynolds et al. |
| 6,088,610 A | 7/2000 | Littmann et al. |
| 6,096,036 A | 8/2000 | Bowe et al. |
| 6,099,524 A | 8/2000 | Lipson et al. |
| 6,106,522 A | 8/2000 | Fleischman et al. |
| 6,107,699 A | 8/2000 | Swanson |
| 6,115,626 A | 9/2000 | Whayne et al. |
| 6,119,041 A | 9/2000 | Pomeranz et al. |
| 6,120,476 A | 9/2000 | Fung et al. |
| 6,129,724 A | 10/2000 | Fleischman et al. |
| 6,141,576 A | 10/2000 | Littmann et al. |
| 6,146,379 A | 11/2000 | Fleischman et al. |
| 6,146,381 A | 11/2000 | Bowe et al. |
| 6,165,169 A | 12/2000 | Panescu et al. |
| 6,167,291 A | 12/2000 | Barajas et al. |
| 6,171,305 B1 | 1/2001 | Sherman |
| 6,171,306 B1 | 1/2001 | Swanson et al. |
| 6,179,833 B1 | 1/2001 | Taylor |
| 6,200,314 B1 | 3/2001 | Sherman |
| 6,212,426 B1 | 4/2001 | Swanson |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,573 B1 | 4/2001 | Webster |
| 6,217,576 B1 | 4/2001 | Tu et al. |
| 6,226,542 B1 | 5/2001 | Reisfeld |
| 6,231,570 B1 | 5/2001 | Tu et al. |
| 6,238,390 B1 | 5/2001 | Tu et al. |
| 6,241,666 B1 | 6/2001 | Pomeranz et al. |
| 6,241,724 B1 | 6/2001 | Fleischman et al. |
| 6,241,725 B1 | 6/2001 | Cosman |
| 6,241,726 B1 | 6/2001 | Chia et al. |
| 6,241,727 B1 | 6/2001 | Tu et al. |
| 6,241,728 B1 | 6/2001 | Gaiser et al. |
| 6,241,754 B1 | 6/2001 | Swanson et al. |
| 6,245,067 B1 | 6/2001 | Tu et al. |
| 6,245,089 B1 | 6/2001 | Daniel et al. |
| 6,251,107 B1 | 6/2001 | Schaer |
| 6,256,540 B1 | 7/2001 | Panescu et al. |
| 6,264,664 B1 | 7/2001 | Avellanet |
| 6,267,746 B1 | 7/2001 | Bumbalough |
| 6,290,697 B1 | 9/2001 | Tu et al. |
| 6,293,943 B1 | 9/2001 | Panescu et al. |
| 6,302,880 B1 | 10/2001 | Schaer |
| 6,309,385 B1 | 10/2001 | Simpson |
| 6,312,391 B1 * | 11/2001 | Ramadhyani et al. ........ 600/549 |
| 6,312,425 B1 | 11/2001 | Simpson et al. |
| 6,319,251 B1 | 11/2001 | Tu et al. |
| 6,325,797 B1 | 12/2001 | Stewart et al. |
| 6,332,880 B1 | 12/2001 | Yang et al. |
| 6,332,881 B1 | 12/2001 | Carner et al. |
| 6,346,104 B2 | 2/2002 | Daly et al. |
| 6,353,751 B1 | 3/2002 | Swanson et al. |
| 6,360,128 B2 | 3/2002 | Kordis et al. |
| 6,370,435 B2 | 4/2002 | Panescu et al. |
| 6,371,955 B1 | 4/2002 | Fuimaono et al. |
| 6,379,352 B1 | 4/2002 | Reynolds et al. |
| 6,389,311 B1 | 5/2002 | Whayne et al. |
| 6,391,024 B1 | 5/2002 | Sun et al. |
| 6,425,894 B1 | 7/2002 | Brucker et al. |
| 6,428,536 B2 | 8/2002 | Panescu et al. |
| 6,428,537 B1 | 8/2002 | Swanson et al. |
| 6,440,129 B1 | 8/2002 | Simpson |
| 6,447,506 B1 | 9/2002 | Swanson et al. |
| 6,451,015 B1 | 9/2002 | Rittman, III et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,693 B1 | 10/2002 | Carroll et al. |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest et al. |
| 6,478,793 B1 | 11/2002 | Cosman et al. |
| 6,485,487 B1 | 11/2002 | Sherman |
| 6,487,441 B1 | 11/2002 | Swanson et al. |
| 6,488,678 B2 | 12/2002 | Sherman |
| 6,490,468 B2 | 12/2002 | Panescu et al. |
| 6,493,586 B1 | 12/2002 | Stahmann et al. |
| 6,500,167 B1 | 12/2002 | Webster, Jr. |
| 6,500,172 B1 | 12/2002 | Panescu et al. |
| 6,514,246 B1 | 2/2003 | Swanson et al. |
| 6,517,536 B2 | 2/2003 | Hoovea et al. |
| 6,522,905 B2 | 2/2003 | Desai |
| 6,529,756 B1 | 3/2003 | Phan et al. |
| 6,540,744 B2 | 4/2003 | Hassett et al. |
| 6,542,773 B2 | 4/2003 | Dupree et al. |
| 6,544,262 B2 | 4/2003 | Fleischman |
| 6,551,271 B2 | 4/2003 | Nguyen |
| 6,554,794 B1 | 4/2003 | Mueller et al. |
| 6,558,378 B2 | 5/2003 | Sherman |
| 6,565,511 B2 | 5/2003 | Panescu et al. |
| 6,569,114 B2 | 5/2003 | Ponzi et al. |
| 6,569,162 B2 | 5/2003 | He |
| 6,569,163 B2 | 5/2003 | Hata et al. |
| 6,572,612 B2 | 6/2003 | Stewart et al. |
| 6,574,492 B1 | 6/2003 | Ben-Haim et al. |
| 6,575,997 B1 | 6/2003 | Palmer et al. |
| 6,583,796 B2 | 6/2003 | Jamar et al. |
| 6,597,955 B2 | 7/2003 | Panescu et al. |
| 6,602,242 B1 | 8/2003 | Fung et al. |
| 6,605,087 B2 | 8/2003 | Swartz et al. |
| 6,607,505 B1 | 8/2003 | Thompson et al. |
| 6,607,520 B2 | 8/2003 | Keane |
| 6,616,657 B2 | 9/2003 | Simpson et al. |
| 6,622,731 B2 * | 9/2003 | Daniel et al. ............... 128/898 |
| 6,625,482 B1 | 9/2003 | Panescu et al. |

(56) References Cited

U.S. PATENT DOCUMENTS

| | | |
|---|---|---|
| 6,628,976 B1 | 9/2003 | Fuimaono et al. |
| 6,632,223 B1 | 10/2003 | Keane |
| 6,635,056 B2 | 10/2003 | Kadhiresan et al. |
| 6,638,223 B2 | 10/2003 | Lifshitz et al. |
| 6,638,275 B1 | 10/2003 | McGaffigan et al. |
| 6,640,120 B1 | 10/2003 | Swanson et al. |
| 6,652,513 B2 | 11/2003 | Panescu et al. |
| 6,652,517 B1 | 11/2003 | Hall et al. |
| 6,669,692 B1 | 12/2003 | Nelson et al. |
| 6,669,693 B2 | 12/2003 | Friedman |
| 6,671,533 B2 | 12/2003 | Chen et al. |
| 6,690,972 B2 | 2/2004 | Conley et al. |
| 6,701,180 B1 | 3/2004 | Desai |
| 6,702,811 B2 | 3/2004 | Stewart et al. |
| 6,711,428 B2 | 3/2004 | Fuimaono et al. |
| 6,730,078 B2 | 5/2004 | Simpson et al. |
| 6,738,673 B2 | 5/2004 | Desai |
| 6,740,080 B2 | 5/2004 | Jain et al. .................. 606/34 |
| 6,743,225 B2 | 6/2004 | Sanchez et al. |
| 6,746,446 B1 | 6/2004 | Hill et al. |
| 6,752,804 B2 | 6/2004 | Sherman |
| 6,761,716 B2 | 7/2004 | Sherman |
| 6,805,131 B2 | 10/2004 | Kordis |
| 6,813,520 B2 | 11/2004 | Sampson et al. |
| 6,814,732 B2 | 11/2004 | Schaer |
| 6,830,576 B2 | 12/2004 | Fleischman et al. |
| 6,866,662 B2 | 3/2005 | Fuimaono et al. |
| 6,893,438 B2 | 5/2005 | Hall et al. |
| 6,893,439 B2 | 5/2005 | Fleischman |
| 6,893,442 B2 | 5/2005 | Whayne |
| 6,916,306 B1 | 7/2005 | Jenkins et al. |
| 6,936,047 B2 | 8/2005 | Nasab et al. |
| 6,939,349 B2 | 9/2005 | Fleischman et al. |
| 6,952,615 B2 | 10/2005 | Satake |
| 6,955,173 B2 | 10/2005 | Lesh |
| 6,960,206 B2 | 11/2005 | Keane |
| 6,961,602 B2 | 11/2005 | Fuimaono et al. |
| 6,964,660 B2 | 11/2005 | Maguire et al. |
| 6,966,908 B2 | 11/2005 | Maguire et al. |
| 6,972,016 B2 | 12/2005 | Hill et al. |
| 6,973,339 B2 | 12/2005 | Govari |
| 6,987,995 B2 | 1/2006 | Drysen |
| 7,001,336 B2 | 2/2006 | Sherman |
| 7,025,766 B2 | 4/2006 | Whayne et al. |
| 7,029,470 B2 | 4/2006 | Francischelli et al. |
| 7,029,471 B2 | 4/2006 | Thompson et al. |
| 7,044,135 B2 | 5/2006 | Lesh |
| 7,047,068 B2 | 5/2006 | Haissaguerre |
| 7,048,734 B1 | 5/2006 | Fleischman et al. |
| 7,048,756 B2 | 5/2006 | Eggers et al. |
| 7,077,823 B2 | 7/2006 | McDaniel |
| 7,094,235 B2 | 8/2006 | Francischelli |
| 7,099,711 B2 | 8/2006 | Fuimaono et al. |
| 7,099,712 B2 | 8/2006 | Fuimaono et al. |
| 7,113,831 B2 | 9/2006 | Hooven |
| 7,115,122 B1 | 10/2006 | Swanson et al. |
| 7,118,568 B2 | 10/2006 | Hassett et al. |
| 7,122,031 B2 | 10/2006 | Edwards et al. |
| 7,151,964 B2 | 12/2006 | Desai |
| 7,155,270 B2 | 12/2006 | Solis et al. |
| 7,156,843 B2 | 1/2007 | Skarda |
| 7,163,537 B2 | 1/2007 | Lee et al. |
| 2001/0008967 A1 | 7/2001 | Sherman |
| 2001/0009976 A1 | 7/2001 | Panescu et al. |
| 2001/0020166 A1 | 9/2001 | Daly et al. |
| 2001/0029366 A1 | 10/2001 | Swanson et al. |
| 2001/0039415 A1 | 11/2001 | Francischelli et al. |
| 2001/0039418 A1 | 11/2001 | Schaer |
| 2001/0044625 A1 | 11/2001 | Hata et al. |
| 2001/0051803 A1 | 12/2001 | Desai |
| 2002/0010392 A1 | 1/2002 | Desai |
| 2002/0065465 A1 | 5/2002 | Panescu et al. |
| 2002/0111548 A1 | 8/2002 | Swanson et al. |
| 2002/0120263 A1 | 8/2002 | Brown et al. |
| 2002/0126036 A1 | 9/2002 | Flaherty et al. |
| 2002/0128643 A1 | 9/2002 | Simpson et al. |
| 2002/0143250 A1 | 10/2002 | Panescu et al. |
| 2002/0161361 A1 | 10/2002 | Sherman |
| 2002/0161422 A1 | 10/2002 | Swanson et al. |
| 2002/0198522 A1 | 12/2002 | Kordis |
| 2003/0018330 A1 | 1/2003 | Swanson et al. |
| 2003/0055419 A1 | 3/2003 | Panescu et al. |
| 2003/0055420 A1 | 3/2003 | Sherman |
| 2003/0060865 A1 | 3/2003 | Desai |
| 2003/0078494 A1* | 4/2003 | Panescu et al. ............... 600/424 |
| 2003/0093069 A1 | 5/2003 | Panescu et al. |
| 2003/0097167 A1* | 5/2003 | Friedman ..................... 607/124 |
| 2003/0125730 A1 | 7/2003 | Berube et al. |
| 2003/0181819 A1 | 9/2003 | Desai |
| 2003/0195407 A1 | 10/2003 | Fuimaono et al. |
| 2003/0195501 A1 | 10/2003 | Sherman |
| 2003/0199746 A1 | 10/2003 | Fuimaono et al. |
| 2003/0199862 A1 | 10/2003 | Simpson et al. |
| 2003/0199868 A1 | 10/2003 | Desai |
| 2003/0204185 A1 | 10/2003 | Sherman |
| 2003/0204186 A1 | 10/2003 | Geistert |
| 2004/0015164 A1 | 1/2004 | Fuimaono et al. |
| 2004/0082947 A1 | 4/2004 | Oral et al. |
| 2004/0097801 A1* | 5/2004 | Mesallum ..................... 600/407 |
| 2004/0116921 A1 | 6/2004 | Sherman et al. |
| 2004/0133154 A1 | 7/2004 | Flaherty et al. |
| 2004/0138545 A1 | 7/2004 | Chen et al. |
| 2004/0143256 A1 | 7/2004 | Bednarek |
| 2004/0152980 A1 | 8/2004 | Desai |
| 2004/0158141 A1 | 8/2004 | Scheib |
| 2004/0181139 A1 | 9/2004 | Falwell et al. |
| 2004/0181249 A1 | 9/2004 | Torrance et al. |
| 2004/0182384 A1 | 9/2004 | Alfery |
| 2004/0236324 A1 | 11/2004 | Muller et al. |
| 2004/0247164 A1 | 12/2004 | Furnish |
| 2005/0010095 A1 | 1/2005 | Stewart et al. |
| 2005/0015084 A1 | 1/2005 | Hill et al. |
| 2005/0033137 A1 | 2/2005 | Oral et al. |
| 2005/0065512 A1 | 3/2005 | Schaer |
| 2005/0096644 A1 | 5/2005 | Hall et al. |
| 2005/0101946 A1 | 5/2005 | Govari et al. |
| 2005/0119651 A1 | 6/2005 | Fuimaono et al. |
| 2005/0148892 A1 | 7/2005 | Desai |
| 2005/0177146 A1 | 8/2005 | Sherman |
| 2005/0187545 A1 | 8/2005 | Hooven et al. .................. 606/41 |
| 2005/0234444 A1 | 10/2005 | Hooven |
| 2005/0240176 A1 | 10/2005 | Oral et al. |
| 2005/0251132 A1 | 11/2005 | Oral et al. |
| 2005/0256521 A1 | 11/2005 | Kozel |
| 2006/0030844 A1 | 2/2006 | Knight et al. |
| 2006/0084966 A1 | 4/2006 | Maguire et al. |
| 2006/0089637 A1 | 4/2006 | Sherman |
| 2006/0095030 A1 | 5/2006 | Avitall et al. |
| 2006/0106375 A1 | 5/2006 | Sherman |
| 2006/0111700 A1 | 5/2006 | Sherman |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2006/0111708 A1 | 5/2006 | Vanney et al. |
| 2006/0122526 A1 | 6/2006 | Berenfeld et al. |
| 2006/0142753 A1 | 6/2006 | Francischelli et al. |
| 2006/0189975 A1 | 8/2006 | Whayne et al. |
| 2006/0195082 A1 | 8/2006 | Francischelli |
| 2006/0206109 A1 | 9/2006 | Swanson |
| 2006/0241366 A1 | 10/2006 | Falwell et al. |
| 2007/0049816 A1 | 3/2007 | Damiano et al. |
| 2007/0083193 A1 | 4/2007 | Werneth et al. |
| 2007/0083194 A1 | 4/2007 | Kunis et al. |
| 2007/0083195 A1 | 4/2007 | Werneth et al. |
| 2007/0106293 A1 | 5/2007 | Oral et al. |

FOREIGN PATENT DOCUMENTS

| | | |
|---|---|---|
| CA | 2327518 | 11/1999 |
| CA | 2328064 | 11/1999 |
| CA | 2328070 | 11/1999 |
| CA | 2371935 | 12/2000 |
| CA | 2222617 C | 7/2002 |
| CA | 2437140 | 6/2004 |

(56) References Cited

FOREIGN PATENT DOCUMENTS

| | | |
|---|---|---|
| CA | 2194061 C | 4/2005 |
| CA | 2492283 | 7/2005 |
| CA | 2276755 C | 5/2006 |
| CA | 2251041 C | 6/2006 |
| EP | 428812 B1 | 3/1995 |
| EP | 779059 A | 6/1997 |
| EP | 0823843 B1 | 2/1998 |
| EP | 0598742 B1 | 8/1999 |
| EP | 0879016 B1 | 10/2003 |
| EP | 1360938 A1 | 11/2003 |
| EP | 1364677 A2 | 11/2003 |
| EP | 1554986 A1 | 7/2005 |
| EP | 1384445 B1 | 2/2006 |
| EP | 1169976 B1 | 4/2006 |
| EP | 1011437 B1 | 5/2006 |
| EP | 1210021 B1 | 5/2006 |
| EP | 1415680 B1 | 5/2006 |
| EP | 1125549 B1 | 6/2006 |
| EP | 1182980 B1 | 6/2006 |
| EP | 1207798 B1 | 6/2006 |
| EP | 1321166 B1 | 7/2006 |
| EP | 1343427 B1 | 7/2006 |
| EP | 1690564 A1 | 8/2006 |
| EP | 0828451 B1 | 9/2006 |
| EP | 1070480 B1 | 9/2006 |
| EP | 1014874 B1 | 12/2006 |
| EP | 1383437 B1 | 12/2006 |
| EP | 1455667 B1 | 1/2007 |
| EP | 1750215 A1 | 2/2007 |
| EP | 957794 B1 | 7/2007 |
| JP | 2004 188179 | 7/2004 |
| SU | 1512622 A1 | 10/1989 |
| SU | 1544396 A1 | 2/1990 |
| SU | 1690786 A1 | 11/1991 |
| WO | WO90/06079 A1 | 6/1990 |
| WO | WO 93/08756 | 12/1993 |
| WO | WO 93/25273 | 12/1993 |
| WO | WO94/12098 A1 | 6/1994 |
| WO | WO96/10961 A1 | 4/1996 |
| WO | WO 96/32885 | 10/1996 |
| WO | WO 96/32897 | 10/1996 |
| WO | WO 96/34558 | 11/1996 |
| WO | WO 96/34559 | 11/1996 |
| WO | WO 96/34560 | 11/1996 |
| WO | WO 96/34567 | 11/1996 |
| WO | WO 96/34569 | 11/1996 |
| WO | WO96/34570 A1 | 11/1996 |
| WO | WO 96/34650 | 11/1996 |
| WO | WO 96/34652 | 11/1996 |
| WO | WO 96/34653 | 11/1996 |
| WO | WO 96/36860 | 11/1996 |
| WO | WO 96/39967 | 12/1996 |
| WO | WO97/15919 A1 | 5/1997 |
| WO | WO 97/17893 | 5/1997 |
| WO | WO97/17904 A1 | 5/1997 |
| WO | WO97/25917 A1 | 7/1997 |
| WO | WO97/25919 A1 | 7/1997 |
| WO | WO97/32525 A1 | 9/1997 |
| WO | WO97/36541 A1 | 10/1997 |
| WO | WO 97/40760 | 11/1997 |
| WO | WO 97/42996 | 11/1997 |
| WO | WO98/18520 A2 | 5/1998 |
| WO | WO98/19611 A1 | 5/1998 |
| WO | WO98/26724 A1 | 6/1998 |
| WO | WO 98/28039 | 7/1998 |
| WO | WO 98/38913 | 9/1998 |
| WO | WO99/02096 A1 | 1/1999 |
| WO | WO 99/56644 | 11/1999 |
| WO | WO 99/56647 | 11/1999 |
| WO | WO 99/56648 | 11/1999 |
| WO | WO 99/56649 | 11/1999 |
| WO | WO 00/78239 | 12/2000 |
| WO | WO02/060523 A2 | 8/2002 |
| WO | WO03/041602 A2 | 5/2003 |
| WO | WO 03/089997 | 10/2003 |
| WO | WO 2005/027765 | 3/2005 |
| WO | WO 2005/027766 | 3/2005 |
| WO | WO2005/065562 A1 | 7/2005 |
| WO | WO2005/065563 A1 | 7/2005 |
| WO | WO 2005/104972 | 11/2005 |
| WO | WO 2006/017517 | 2/2006 |
| WO | WO 2006/044794 | 4/2006 |
| WO | WO2006/049970 A2 | 5/2006 |
| WO | WO 2006/052651 | 5/2006 |
| WO | WO 2006/052905 | 5/2006 |
| WO | WO 2006/055654 | 5/2006 |
| WO | WO 2006/055658 | 5/2006 |
| WO | WO 2006/055733 | 5/2006 |
| WO | WO 2006/055741 | 5/2006 |

OTHER PUBLICATIONS

Werneth et al.; U.S. Appl. No. 12/245,625 entitled "Ablation catheter,", filed Oct. 3, 2008.
Oral et al., "Catheter ablation for paroxysmal atrial fibrillation: segmental pulmonary vein ostial ablation versus left atrial ablation," Circulation, vol. 108, pp. 2355-2360, 2003.
Oral et al., "Segmental ostial ablation to isolate the pulmonary veins during atrial fibrillation: feasibility and mechanistic insights," Circulation, vol. 106, pp. 1256-1262, 2002.
Nademanee et al., "A new approach for catheter ablation of atrial fibrillation: mapping of the electrophysiologic substrate," JACC, vol. 43, No. 11, pp. 2044-2053, 2004.
Wittkampf et al., "Radiofrequency ablation with a cooled porous electrode catheter," (abstract) JACC, vol. 11, No. 2, pp. 17a, Feb. 1988.
Oral et al.; U.S. Appl. No. 11/932,378 entitled "Ablation catheters and methods for their use," filed Oct. 31, 2007.
Werneth et al.; U.S. Appl. No. 12/116,753 entitled "Ablation therapy system and method for treating continuous atrial fibrillation," filed May 7, 2008.
Sherman et al.; U.S. Appl. No. 12/117,596 entitled RF energy delivery system and method, filed May 8, 2008.
Oral et al.; U.S. Appl. No. 12/176,115 entitled "Atrial ablation catheter adapted for treatment of septal wall arrhythmogenic foci and method of use," filed Jul. 18, 2008.

* cited by examiner

ABLATION SYSTEM WITH FEEDBACK

STATEMENT OF RELATED APPLICATIONS

This application claims the benefit of priority of U.S. Provisional Patent Application No. 60/628,090, filed Nov. 15, 2004, entitled "Ablation System With Feedback," which is incorporated by reference herein in its entirety.

FIELD OF THE INVENTION

Field of the Invention

The present invention relates generally to systems, catheters and methods for performing targeted tissue ablation in a subject. In particular, the present invention provides a system including an ablation catheter, an esophageal probe, and an interface unit for providing energy to the ablation catheter. The ablation catheters have distal ends configured to treat two dimensional regions of target tissue, including deployable distal ends, and methods for treating conditions (e.g., cardiac arrhythmias) with these and similar devices.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia. Often the ablation is performed by passing energy, such as electrical energy, through one or more electrodes causing the tissue in contact with the electrodes to heat up to an ablative temperature. Ablation procedures can be performed on patients with atrial fibrillation by ablating tissue in the heart.

Mammalian organ function typically occurs through the transmission of electrical impulses from one tissue to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria instead of only from the sinus node. This overwhelms the atrioventricular node into producing an irregular and rapid heartbeat. As a result, blood pools in the atria that increases a risk for blood clot formation. The major risk factors for atrial fibrillation include age, coronary artery disease, rheumatic heart disease, hypertension, diabetes, and thyrotoxicosis. Atrial fibrillation affects 7% of the population over age 65.

Atrial fibrillation treatment options are limited. Lifestyle change only assists individuals with lifestyle related atrial fibrillation. Medication therapy assists only in the management of atrial fibrillation symptoms, may present side effects more dangerous than atrial fibrillation, and fail to cure atrial fibrillation. Electrical cardioversion attempts to restore sinus rhythm but has a high recurrence rate. In addition, if there is a blood clot in the atria, cardioversion may cause the clot to leave the heart and travel to the brain that may lead to stroke, or to some other part of the body. What are needed are new methods for treating atrial fibrillation and other conditions involving disorganized electrical conduction.

Various ablation techniques have been proposed to treat atrial fibrillation, including the Cox-Maze procedure, linear ablation of various regions of the atrium, and circumferential ablation of pulmonary vein ostia. The Cox-Maze procedure is a complex, invasive, surgical procedure with a long procedure and recovery time. Pulmonary vein ostial ablation is proving to be difficult to do, and has lead to rapid stenosis and potential occlusion of the pulmonary veins. Atrial ablation procedures have the risk of damaging neighboring tissue such as the esophagus. There is therefore a need for improved atrial ablation systems, devices and techniques.

SUMMARY OF THE INVENTION

According to a first aspect of the invention, an ablation system used by an operator to treat a patient with an arrhythmia is disclosed. The system includes an esophageal probe that is placed in the esophagus of the patient. The esophageal probe comprises a flexible shaft which a proximal end, a distal end, and an exterior wall. The probe further includes a first location element. The system further includes an ablation catheter that includes at least one ablation element for delivering energy to cardiac tissue. The ablation catheter comprises a flexible shaft with a proximal and, a distal end, and an exterior wall. The catheter further comprises a second location element. The system further includes an interface unit for providing energy to the ablation catheter. Calculating means determines the distance between the first location element and the second location element.

In a preferred embodiment of the ablation system of the present invention, the esophageal probe includes a temperature sensor, and the distance determined by the calculating means is used in combination with the temperature measured by the temperature sensor to set or modify one or more system parameters, such as a temperature threshold used by the system to modify delivery of energy to tissue. In another preferred embodiment, the type or mode of energy delivery is modified based on the calculated distance and/or the temperature received by a temperature sensor. Changing the mode of energy delivered may include a change from monopolar RF energy delivery to bipolar RF energy delivery, such as to decrease depth of heat penetration. Numerous forms of energy can be used to ablate tissue including but not limited to: sound energy such as acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof.

In another preferred embodiment of the ablation system of the present invention, the interface unit includes an imaging interface such as an ultrasound monitor. Alternatively or additionally, the interface unit may provide an analysis function such as the calculating means of the present invention; and or an analysis function to determine an ablation setting such as: a energy delivery amount; an energy delivery frequency; an energy delivery voltage; an energy delivery current; an energy delivery temperature; an energy delivery rate; an energy delivery duration; an energy delivery modulation parameter; an energy threshold; another energy delivery parameter; a temperature threshold; an alarm threshold; another alarm parameter; and combinations thereof.

In another preferred embodiment of the ablation system of the present invention, either the first location element or the second location element is a transmitting antenna and the other location element is a receiving antenna. The calculating means utilizes properties of the transmitted and/or received signals to determine the distance between the first location element and the second location element. Transmitting signals may included electromagnetic waves, sound signals such as ultrasound signals, light signals or other types of signals. In another preferred embodiment, either or both the first location element and the second location element are radiographic markers, and x-ray such as fluoroscopy transmissions are used to determine the distance between the first location element and the second location element. In another preferred embodiment, either the first location element or the second location element is an ultrasound transducer such as an ultrasound catheter inserted into a lumen of either or both the esophageal probe or the ablation catheter.

In another preferred embodiment of the ablation system of the present invention, either the esophageal probe or the ablation catheter further comprises on or more functional elements such as: a sensor; an energy transmitter; a signal transmitter; an imaging element; and combinations thereof. Numerous sensors can be included as functional elements integrated into either the esophageal probe or the ablation catheter such as: an electrical signal sensor such as a cardiac electrode; a temperature sensor such as a thermocouple; an imaging transducer such as an array of ultrasound crystals; a pressure sensor; a pH sensor; a physiologic sensor such as a blood sensor; a respiratory sensor; an EEG sensor; a pulse oximetry sensor; a blood glucose sensor; an impedance sensor; a contact sensor; a strain gauge; an acoustic sensor; and combinations thereof. Numerous sensors can be included as functional elements integrated into either the esophageal probe or the ablation catheter such as: a pacing electrode; a defibrillation electrode; other electrodes configured to generate electrical signals that modify the cardiac function of the patient; and other transmitters. Electrodes may consist of a plate or a coil; and may have a geometry consisting of a flat or a dome-like protuberance. Electrodes can also be an annular ring around a segment of a tubular structure portion of either the esophageal probe or the ablation catheter. Electrodes can also be integrated into an expandable balloon, expandable from the shaft of the device.

An imaging transducer, such as an ultrasound transducer can be included as functional elements integrated into either the esophageal probe or the ablation catheter. Multiplexing elements may be integrated into the esophageal probe and/or ablation catheter, such as elements that multiplex signals and/or power to or from one or more functional elements of the device. In a preferred embodiment, the multiplexing elements multiplex drive signals to two or more ablation elements of the ablation catheter. Deflecting means may be integrated into the esophageal probe and/or ablation catheter, such as deflecting means comprising a mechanical linkage extending from a proximal location external to the patient and a point near the distal end of the flexible shaft of the device. The deflecting means is preferably utilized to deflect one or more functional elements to be in contact with tissue. Deflecting means may also include a balloon near the distal end of a flexible shaft wherein inflation of the balloon deflects a portion of an exterior wall of the flexible shaft to be in contact with tissue.

In a preferred embodiment of the ablation system of the present invention, a carrier assembly may be provided in the ablation catheter and/or esophageal probe for providing functional elements, such as electrodes or temperature sensors, in a resiliently biased configuration. The carrier assembly is attached to a control shaft whose advancement deploys the carrier assembly from a constrained condition within a lumen of the device to an expanded condition. The carrier assembly may include wires, ribbons, cables and struts, made of metals, non-metals or combinations of both. In a preferred embodiment, the carrier assembly includes multiple types of functional elements such as ablation electrodes and sensors. The carrier assembly may be deployed through advancement of the control shaft by exiting the distal end of a flexible shaft or a side hole of the flexible shaft.

In another aspect of the present invention, an ablation system for an operator to treat a patient with arrhythmia is disclosed. The system includes an ablation catheter comprising at least one ablation element for delivering energy to cardiac tissue. The ablation catheter includes a proximal end, a distal end and an exterior wall. The system further includes an interface unit for providing energy to the ablation catheter. An esophageal probe for placing in the esophagus of the patient is also included. The esophageal probe includes a proximal end, a distal end, an exterior wall and a location element. Calculating means determine the distance between the location element of the esophageal probe and at least one of the ablation elements of the ablation catheter.

In another aspect of the present invention, an ablation system for an operator to treat a patient with arrhythmia is disclosed. The system includes an ablation catheter comprising at least one ablation element for delivering energy to cardiac tissue. The ablation catheter includes a proximal end, a distal end, an exterior wall and a location element. The system further includes an interface unit for providing energy to the ablation catheter. An esophageal probe for placing in the esophagus of the patient is also included. The esophageal probe includes a proximal end, a distal end, an exterior wall and a sensor. Calculating means determine the distance between the location element of the ablation catheter and the sensor of the esophageal probe.

In another aspect of the present invention, an esophageal probe is disclosed. The esophageal probe includes an elongate member adapted to be positioned within the esophagus of a patient. The probe includes a proximal end, a distal end, and an exterior wall. A sensor is located near the distal end of the probe. The esophageal probe further includes a visualization transducer at a location near the sensor. In a preferred embodiment, the sensor is a temperature sensor and the visualization transducer is an ultrasound transducer such as an ultrasound transducer integral to an ultrasound catheter inserted within a lumen of the esophageal probe. In another preferred embodiment, the sensor is selected from the group consisting of: an electrical signal sensor such as a cardiac electrode; a temperature sensor such as a thermocouple; an imaging transducer such as an array of ultrasound crystals; a pressure sensor; a pH sensor; a physiologic sensor such as a blood sensor, a respiratory sensor; an EEG sensor, a pulse oximetry sensor and a blood glucose sensor; an impedance sensor; a contact sensor; a strain gauge; an acoustic sensor; and combinations thereof.

In another aspect of the present invention, a method of treating a patient with arrhythmia is disclosed. An ablation system is provided comprising an esophageal probe, an ablation catheter and an interface unit. The esophageal probe is for placing in the esophagus of the patient, and includes an elongate shaft with a proximal end, a distal end, an exterior wall and a location element. The ablation catheter includes at least one ablation element for delivering energy to cardiac tissue. The catheter further comprises a flexible shaft with a proximal end, a distal end and an exterior wall. Calculating means are for determining the distance between the location element of the esophageal probe and an ablation element of the ablation catheter. This distance is calculated utilizing the calculating means and a system parameter is set based on the value of the distance. Energy is then delivered to cardiac tissue.

Both the foregoing general description and the following detailed description are exemplary and are intended to provide further explanation of the embodiments of the invention as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIG. 7a illustrates a front cut-away anatomic view of the esophageal probe of the present invention placed in the esophagus of a patient.

FIG. 7b illustrates a sectional view of the torso of a patient with the ablation catheter placed in the left atrium and the esophageal probe in the esophagus.

DESCRIPTION OF THE EMBODIMENTS

Figure 1:
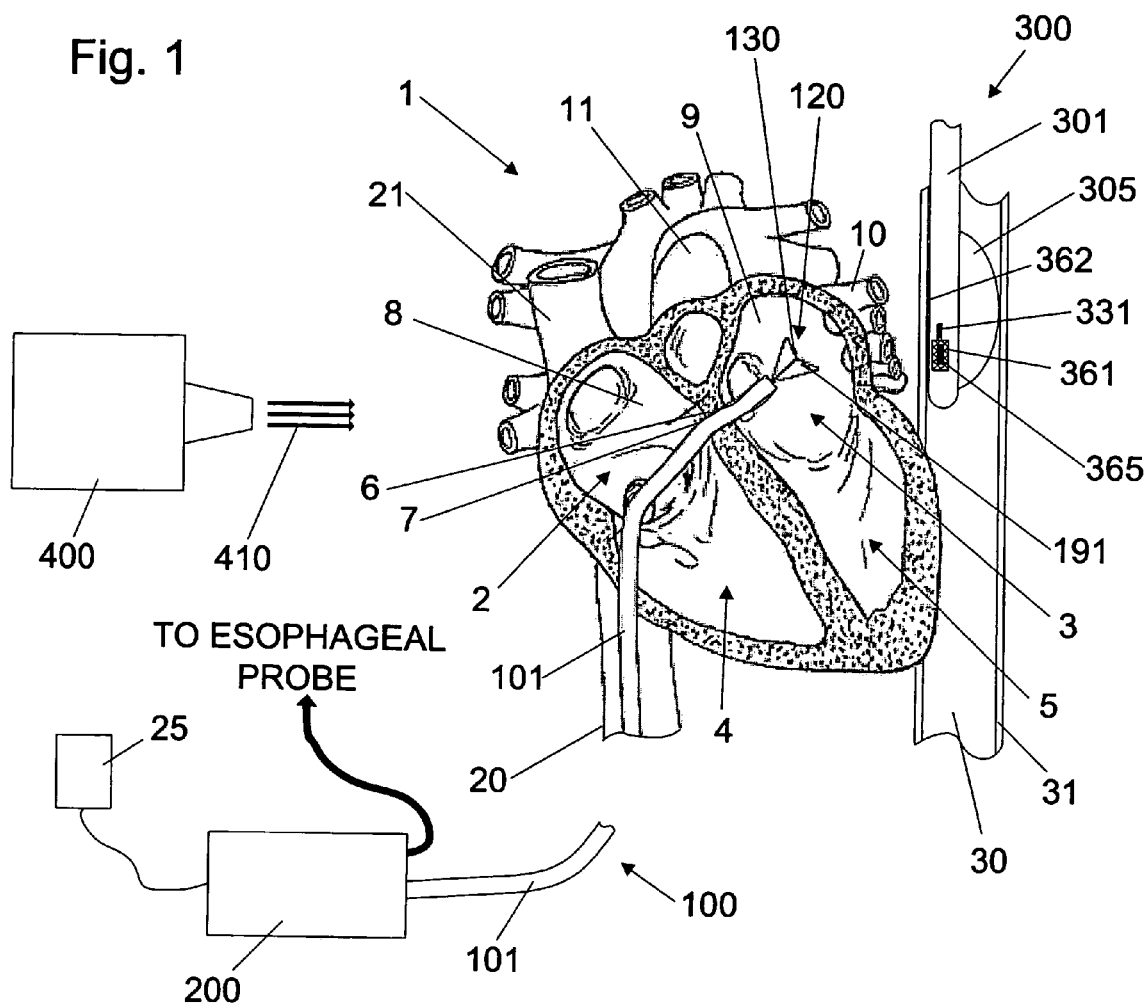
FIG. 1 illustrates the system of the present invention and the treatment to be accomplished with the devices and methods described below.

Reference will now be made in detail to the present embodiments of the invention, examples of which are illustrated in the accompanying drawings. Wherever possible, the same reference numbers will be used throughout the drawings to refer to the same or like parts.

The present invention provides a system, devices and methods for performing targeted tissue ablation in a subject. In preferred embodiments, the system provides multiple devices to allow an operator to treat a patient with arrhythmia. The system includes an esophageal probe that is placed in the esophagus of the patient. The probe comprises a flexible shaft with a proximal end, a distal end and an exterior wall, as well as a location element preferably mounted near its distal end. An ablation catheter includes at least one ablation element for delivering energy to cardiac tissue. The catheter comprises a flexible shaft with a proximal end, a distal end and an exterior wall, as well as a location element preferably mounted near its distal end. Further included in the system is an interface unit that is configured to deliver one or more forms of energy to the ablation elements of the ablation catheter. The system further includes calculating means that determine or are used to determine the distance between the esophageal probe location element and the ablation catheter location element. In a preferred embodiment, the esophageal probe location element is in close proximity to a temperature sensor, and the ablation catheter location element is in close proximity to an ablation element.

The esophageal probe is preferably of the type for performing esophageal procedures or monitoring, and can be introduced through the mouth or nose to the esophagus. The probe preferably includes at least one temperature sensor to monitor the temperature of one or more portions of the esophageal wall. The ablation catheter is preferably of the type used for performing intracardiac procedures, typically being introduced from the femoral vein in a patient's leg. The catheter is preferably introducable through an access sheath and also preferably has a steerable tip that allows positioning of the distal portion such as when the distal end of the catheter is within a heart chamber. The catheters include ablation elements that may be mounted on a carrier assembly. The carrier assembly is attached to a coupler, which in turn is connected to a control shaft that is coaxially disposed and slidingly received within the lumen of the tubular body member. The carrier assembly is deployable from the distal end of the tubular body member by advancing the control shaft, such as to allow the carrier assembly to resiliently expand and engage one or more ablation elements against cardiac tissue, typically atrial wall tissue or other endocardial tissue. Retraction of the control shaft causes the carrier assembly to be constrained within the lumen of the tubular body member. The ablation element carrying carrier assembly, when deployed and flattened against an endocardial surface, is preferably about 15 to 30 mm in diameter, which arm segments of the carrier assembly about 7 to 15 mm long. The wire width of the carrier assembly re preferably about 0.26 mm. Carrier assemblies can include other functional elements in addition to ablation electrodes, such as temperature sensors when a carrier assembly is integral to the esophageal probe.

Arrays of ablation elements, preferably electrode arrays, may be configured in a wide variety of ways and patterns. In particular, the present invention provides devices with electrode arrays that provide electrical energy, such as radiofrequency (RF) energy, in monopolar (unipolar), bipolar or phased monopolar-bipolar fashion, as well as methods for treating conditions (e.g., atrial fibrillation, supra ventricular tachycardia, atrial tachycardia, ventricular tachycardia, ventricular fibrillation, and the like) with these devices. Alternative to or in combination with ablation elements that deliver electrical energy to tissue, other forms and types of energy can be delivered including but not limited to: sound energy such as acoustic energy and ultrasound energy; electromagnetic energy such as electrical, magnetic, microwave and radiofrequency energies; thermal energy such as heat and cryogenic energies; chemical energy such as energy generated by delivery of a drug; light energy such as infrared and visible light energies; mechanical and physical energy; radiation; and combinations thereof.

As described above, the normal functioning of the heart relies on proper electrical impulse generation and transmission. In certain heart diseases (e.g., atrial fibrillation) proper electrical generation and transmission are disrupted or are otherwise abnormal. In order to prevent improper impulse generation and transmission from causing an undesired condition, the ablation catheters of the present invention may be employed.

One current method of treating cardiac arrhythmias is with catheter ablation therapy. Physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician) directs a catheter through a main vein or artery into the interior region of the heart that is to be treated. The ablating element is next placed near the targeted cardiac tissue that is to be ablated. The physician directs energy, provided by a source external to the patient, from one ore more ablation elements to ablate the neighboring tissue and form a lesion. In general, the goal of catheter ablation therapy is to disrupt the electrical pathways in cardiac tissue to stop the emission of and/or prevent the propagation of erratic electric impulses, thereby curing the heart of the disorder. For treatment of atrial fibrillation, currently available methods and devices have shown only limited success and/or employ devices that are extremely difficult to use or otherwise impractical.

The ablation catheters of the present invention allow the generation of lesions of appropriate size and shape to treat conditions involving disorganized electrical conduction (e.g., atrial fibrillation). The system of the present invention is practical in terms of ease-of-use and limiting risk to the patient, as well as significantly reducing procedure times. The present invention addresses this need with, for example, spiral shaped and radial arm shaped (also called umbrella shaped) carrier assemblies whose ablation elements create spiral, radial, or other simple or complex shaped patterns of lesions in the endocardial surface of the atria by delivery of energy to tissue or other means. The lesions created by the ablation catheters are suitable for inhibiting the propagation of inappropriate electrical impulses in the heart for prevention of reentrant arrhythmias. The esophageal probe and calculating means, can be used to safely control ablative energy delivery through limiting the temperature created in tissue neighboring the tissue to be ablated.

Definitions. To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited to, individuals requiring medical assistance, and in particular, requiring atrial fibrillation catheter ablation treatment.

As used herein, the terms "catheter ablation" or "ablation procedures" or "ablation therapy," and like terms, refer to what is generally known as tissue destruction procedures. Ablation is often used in treating several medical conditions, including abnormal heart rhythms. It can be performed both surgically and non-surgically. Non-surgical ablation is typically performed in a special lab called the electrophysiology (EP) laboratory. During this non-surgical procedure a catheter is inserted into the heart using fluoroscopy for visualization, and then an energy delivery apparatus is used to direct energy to the heart muscle. This energy either "disconnects" or "isolates" the pathway of the abnormal rhythm (depending on the type of ablation). It can also be used to disconnect the conductive pathway between the upper chambers (atria) and the lower chambers (ventricles) of the heart. For individuals requiring heart surgery, ablation can be performed during coronary artery bypass or valve surgery.

As used herein, the term "functional element" refers to a component that performs a specific function relative to the procedure being formed. Typical examples of functional elements include sensors and transmitters.

As used herein, the term "ablation element" refers to a functional element that delivers energy to ablate tissue, such as an electrode for delivering electrical energy. Ablation elements can be configured to deliver multiple types of energy, such as ultrasound energy and cryogenic energy, either simultaneously or serially. Electrodes can be constructed of a conductive plate, wire coil, or other means of conducting electrical energy through contacting tissue. In monopolar energy delivery, the energy is conducted from the electrode, through the tissue to a ground pad, such as a conductive pad attached to the back of the patient. The high concentration of energy at the electrode site causes localized tissue ablation. In bipolar energy delivery, the energy is conducted from a first electrode to one or more separate electrodes, relatively local to the first electrode, through the tissue between the associated electrodes. Bipolar energy delivery results in more precise, shallow lesions while monopolar delivery results in deeper lesions. Both monopolar and bipolar delivery provide advantages, and the combination of their use is a preferred embodiment of this application. Energy can also be delivered using pulse width modulated drive signals, well known to those of skill in the art. Energy can also be delivered in a closed loop fashion, such as a system with temperature feedback wherein the temperature modifies the type, frequency and or magnitude of the energy delivered.

As used herein, the term "carrier assembly" refers to a flexible carrier, on which one or more functional elements, such as ablation elements are disposed. A carrier assembly provides these functional elements in a resiliently biased configuration. The carrier assembly is a support structure that is shiftable from a storage or confined configuration, such as a radially constrained configuration, to a deployed or expanded configuration. The carrier assembly can include wires, ribbons, cables and/or struts and is constructed of metals, non-metals or combinations of both. Typical metals chosen for carrier assembly construction include but are not limited to: stainless steel, Nitinol™, Elgiloy™, other alloys and combinations thereof. Carrier assemblies are not limited to any particular size or shape, and can be constrained within an appropriately sized lumen.

As used herein, the term "spiral tip" refers to a carrier assembly configured in its fully expanded state into the shape of a spiral. The spiral tip is not limited in the number of spirals it may contain. Examples include, but are not limited to, a wire tip body with one spiral, two spirals, ten spirals, and a half of a spiral. The spirals can lie in a relatively single plane, or in multiple planes. A spiral tip may be configured for energy delivery during an ablation procedure.

As used herein the term "umbrella tip" refers to a carrier assembly with a geometric center which lies at a point along the axis of the distal portion of the tubular body member, with one or more bendable or hinged carrier arms extending from the geometric center, in an umbrella configuration. Each carrier arm may include one or more ablation elements. Each carrier arm of an umbrella tip includes a proximal arm segment and a distal arm segment, the distal arm segment more distal than the proximal arm segment when the carrier assembly is in a fully expanded condition. One or more additional carrier arms can be included which include no ablation elements, such as carrier arms used to provide support or cause a particular deflection. An umbrella tip body is not limited to any particular size. An umbrella tip may be configured for energy delivery during an ablation procedure.

As used herein, the term "lesion," or "ablation lesion," and like terms, refers to tissue that has received ablation therapy. Examples include, but are not limited to, scars, scabs, dead tissue, burned tissue and tissue with conductive pathways that have been made highly resistive or disconnected.

As used herein, the term "spiral lesion" refers to an ablation lesion delivered through a spiral tip ablation catheter. Examples include, but are not limited to, lesions in the shape of a wide spiral, and a narrow spiral, a continuous spiral and a discontinuous spiral.

As used herein, the term "umbrella lesion" or "radial lesion," and like terms, refers to an ablation lesion delivered through an umbrella tip ablation catheter. Examples include, but are not limited to, lesions with five equilateral prongs extending from center point, lesions with four equilateral prongs extending from center point, lesions with three equilateral prongs extending from center point, and lesions with three to five non-equilateral prongs extending from center point.

As used herein, the term "coupler" refers to an element that connects the carrier assembly to the control shaft. Multiple shafts, or ends of the carrier assembly may connect to the coupler. Multiple carrier arms can have one or more of their ends attached to the coupler. The coupler may include antirotation means that work in combination with mating means in the tubular body member. Couplers may be constructed of one or more materials such as polyurethane, steel, titanium, and polyethylene.

As used herein, the term "carrier arm" refers to a wire-like shaft capable of interfacing with electrodes and the coupler. A carrier arm is not limited to any size or measurement. Examples include, but are not limited to: stainless steel shafts; Nitinol™ shafts; titanium shafts; polyurethane shafts; nylon shafts; and steel shafts. Carrier arms can be entirely flexible, or may include flexible and rigid segments.

As used herein, the term "carrier arm bend portion" refers to a joint (e.g., junction, flexion point) located on a carrier arm. The degree of flexion for a carrier arm bend portion may range from 0 to 360 degrees. The bend portion can be manufactured such what when the carrier assembly is fully expanded the bend point is positioned in a relatively straight portion, a curved portion, or in a discrete transition from a first direction to a second transition, such as a 45 degree bend transition. The bend portion can include one or more flexing means such as a spring, a reduced diameter segment, or a segment of increased flexibility.

The present invention provides structures that embody aspects of the ablation catheter. The present invention provides structures that embody aspects of the esophageal probe. The present invention also provides tissue ablation systems and methods for using such ablation systems. The illustrated and preferred embodiments discuss these structures and techniques in the context of catheter-based cardiac ablation. These structures, systems, and techniques are well suited for use in the field of cardiac ablation.

The multifunctional ablation catheters, esophageal probes, ablation systems and methods of the present invention have advantages over previous prior art systems, devices and methods. FIGS. 1-8 show various preferred embodiments of the systems, methods and devices of the present invention. The present invention is not limited to these particular configurations.

FIG. 1 illustrates the treatment to be accomplished with the devices and methods described herebelow wherein an ablation catheter includes a location element integral to its structure and an esophageal probe includes a location element integral to its structure. An X-ray unit is also provided for determining the distance between the two location elements, the distance being used to determine the value of one or more parameters of the system. FIG. 1 shows a cutaway view of the human heart 1 showing the major structures of the heart including right atrium 2, left atrium 3, right ventricle 4, and left ventricle 5. Atrial septum 6 separates left atrium 3 and right atrium 2. Fossa ovalis 7 is a small depression in the atrial septum that may be used as an access pathway to the left atrium from the right atrium. Fossa ovalis 7 can be punctured, and easily reseals and heals after procedure completion. In a patient suffering from atrial fibrillation, aberrant electrically conductive tissue may be found in the atrial walls 8 and 9, as well as in the pulmonary veins 10 and the pulmonary arteries 11. Ablation of these dysfunctional areas, referred to as arrhythmogenic foci (also referred to as drivers or rotors), is an effective treatment for atrial fibrillation. Though circumferential ablation of the pulmonary veins can cure the arrhythmia that originates in the pulmonary veins, it may result in eventual stenosis of these pulmonary veins, a very undesirable condition. The system of the present invention provides means of creating lesions remote from these pulmonary veins and their ostia while being easily deployed to ablate the driver and rotor tissue without causing unnecessary tissue damage to the heart and neighboring tissues and structures.

To accomplish the lesion creation, ablation catheter 100 is inserted into the right atrium 2, preferably through the inferior vena cava 20 as shown in the illustration, via femoral vein access, or through the superior vena cava 21. Catheter 100 may include an integral sheath, such as a tip deflecting sheath, or may work in combination with a separate sheath. When passing into left atrium 3, catheter 100 passes through or penetrates the fossa ovalis 7, such as over a guide wire previously placed using a trans-septal puncture device, not shown. Catheter 100 includes carrier assembly 120, which is a flexible structure, shown in an umbrella configuration, with one or more ablation elements, such as heat generating RF electrodes 130. Carrier assembly is a wire-like structure constructed of one or more flexible materials including but not limited to: Nitinol; stainless steel; nylon; and combinations thereof. In an alternative embodiment, carrier assembly 120 can have an expanded state with different geometries such as spiral shaped geometries. Carrier assembly 120 is shown extending beyond the distal end of catheter shaft 101 of catheter 100. Carrier assembly 120 is adapted to be deformable such that pressing carrier assembly into left atrial wall 9 will cause one or more and preferably all of electrodes 130 to make contact with the tissue to be analyzed and/or ablated. Each of the electrodes 130 is attached via connecting wires, not shown, that extend proximally and electrically attach to an interface unit of the system of the present invention. The interface unit of FIG. 1, RF delivery unit 200, provides at least RF energy to ablation catheter 100.

RF delivery unit 200 and ablation catheter 100 are configured to delivery RF energy in monopolar, bipolar or combination monopolar-bipolar energy delivery modes. Patch electrode 25, preferably a conductive pad attached to the back of the patient, is used to deliver monopolar RF energy from electrodes 130. In a preferred embodiment, monopolar energy delivery is followed by bipolar energy delivery, which is then followed a period without energy delivery, such as a sequence in which the three steps have equal durations. In another preferred embodiment, RF delivery unit 200 is configured to also provide electrical mapping of the tissue that is contacted by one or more electrodes integral to carrier assembly 120. Electrodes 130 can be configured to be mapping electrodes and/or additional mapping only electrodes can be integral to carrier assembly 120 to provide the cardiac signal mapping function. Carrier assembly 120 is configured to engage an endocardial surface to map and/or ablate tissue on the surface. In a preferred method, RF energy is delivered after a proper location of the electrodes 130 is confirmed with a mapping procedure. If the position is determined to be inadequate, carrier assembly 120 is repositioned through various manipulations performed at the proximal end of the ablation catheter 100 by an operator. In another preferred embodiment, RF delivery unit 200 is configured to deliver both RF energy and ultrasound energy to the identical or different electrodes 130. In another preferred embodiment, RF delivery unit 200 is configured to accept a signal from one or more sensors integral to ablation catheter 100, not shown, such that the energy delivered can be modified via an algorithm which processes the information received from the one or more sensors.

The system of FIG. 1 further includes esophageal probe 300, inserted into esophagus 30 of the patient. Probe 300 is advanced into the esophagus, such as via the mouth or nose of the patient and performed under fluoroscopy, to a location in proximity to the cardiac tissue to be ablated. Probe 300 includes a flexible shaft, shaft 301, which includes a temperature sensor, thermocouple 361, on the outer surface and near the distal end of shaft 301. Thermocouple 361 is covered by membrane 365, preferably a flexible structure such as an elastomeric membrane. Wires are connected to thermocouple 361 and extend proximally to the proximal end of probe 300, wires and proximal end not shown, such that the temperature at thermocouple 361 can be determined by signals transmitted to and/or from thermocouple 361 via the wires. The electronics necessary to transmit and/or receive the signals and determine the temperature may be integral to a handle, also not shown, on the proximal end of probe 300 and/or a separate device attached to a connector in electrical communication with the wires.

Esophageal probe 300 further includes balloon 305, such as a compliant or non-compliant balloon. Probe 300 includes an inflation port on its proximal end, and a lumen, both not shown, the lumen extending from the inflation port to the balloon such that balloon can be controllably inflated and deflated. Balloon 305 is located near the distal end of shaft 301 in close proximity to thermocouple 361 and radiopaque marker 331, such as at the same longitudinal position but eccentrically configured on the opposite side of shaft 301. In an alternative embodiment, balloon 305 is concentric with shaft 301. During the procedure, balloon 305 is rotationally oriented by torquing the proximal end of shaft 301. In a preferred method, balloon 305 is positioned such that when balloon 305 is inflated and contact between balloon 305 and esophageal wall 31 causes membrane 365 to contact the contralateral wall, thermocouple 361 is positioned in relatively the closest location within esophagus 30 to the intended heart tissue to be ablated. A functional element, such as a transducer or sensor not shown, can be mounted on the exterior surface of the balloon, such that when the balloon 305 is inflated, the functional element is in contact with esophageal wall 31. In a preferred embodiment, the functional element is a thermocouple. Additionally or alternatively to probe 300, catheter 100 may include a balloon, as well as a balloon inflation lumen and an inflation port. A balloon integral to catheter 100 may be concentric or eccentric with shaft 101, and may include one or more functional elements. The integral balloons may have a cross-sectional profile, or be positioned on the shaft, such as to avoid occlusion of the structure in which the balloon is inflated. A pressure sensor may be in fluid communication with the inflation lumen of the balloon to help prevent over-pressurization of the balloon, to avoid damage to the esophagus or other tissue.

Figure 2:
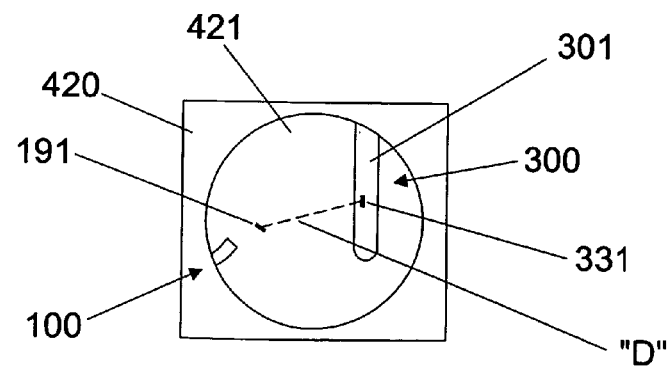
FIG. 2 illustrates a front view of the X-ray screen of the system of FIG. 1

Insertion and positioning of ablation catheter 100 and esophageal probe 300 is performed under x-ray visualization such as fluoroscopy provided by x-ray unit 400. Referring additionally to FIG. 2, catheter 100 includes a location element, radiographic marker 191 preferably mounted in close proximity to one or more electrodes 130, and probe 300 includes a location element, radiographic marker 331, preferably mounted in close proximity to thermocouple 361. In an alternative embodiment, one or more electrodes 130 of catheter 100 can be made of radiopaque material obviating the need for radiopaque marker 191. In another alternative embodiment, thermocouple 361 or membrane 365 can include radiopaque materials obviating the need for radiographic marker 331. Radiographic markers, well known to those of skill in the art, may include radiopaque metals such as platinum, or radiopaque additives included in the extrusion materials of flexible catheter bodies, such as Barium Sulfate. In an alternative embodiment, shaft 301 is radiopaque, the entire shaft facilitating as a location element, obviating the need for radiographic marker 331. In another preferred method, probe 300 is rotationally oriented when balloon 305 is deflated or partially deflated, and one or more measurements are taken using visualization means such as x-ray unit 400 to minimize the distance between radiopaque marker 331 of probe 300 and radiopaque marker 191 of catheter 100. Referring specifically to FIG. 2, X-Ray monitor 420 includes screen 421 which is positioned to be visualized by the operator during the performance of the ablation procedure. In a preferred method, a bi-plane fluoroscopy unit is utilized, including a second display screen providing images from a second X-ray source.

During the procedure, the X-ray source is positioned such that the distance between radiographic marker 331 of probe 300 and radiographic marker 191 of catheter 100 is displayed at its maximum value. This maximum value is displayed when X-ray beams 410 are perpendicular to the line between the two markers. In a preferred method, the one or more X-ray generators are continuously maneuvered through various positions, until the maximum separation distance is visualized. This maximum distance, distance D, is manually calculated by the operator or other assisting personnel in the procedure room, and can be used by the system of the present invention to perform one or more functions such as setting a maximum temperature in the esophagus to be sensed by thermocouple 361. In a preferred embodiment, ablation catheter 100 and/or esophageal probe 300 includes a portion of known dimensions, such that distance D can be calculated in proportion to one or more known dimensions. In alternative embodiments, described in detail in reference to subsequent figures, distance D is automatically calculated by one or more components of the system, such as the interface unit, RF delivery unit 200. Since tissue damage to the esophagus should be avoided, as well as damage to heart or other tissue that is not a cause of the patient's arrhythmia, it is desirable for such a temperature threshold to be inversely proportional to the distance between thermocouple 361 and the electrodes of ablation catheter 100.

In a preferred embodiment, when the temperature sensed by thermocouple 361 reaches one or more pre-determined thresholds, the energy being delivered is modified. The modification can include changing the type or types of energy delivered such as from RF to microwave energies; changing the intensity of energy delivered including a stoppage of energy delivery; changing the frequency of energy delivered;

changing a pulse width modulation parameter of energy delivered including changing monopolar and bipolar delivery on and off times; and combinations thereof. In another preferred embodiment, phased monopolar-bipolar delivery is changed to bipolar delivery. In another preferred embodiment, when the sensed temperature reaches a threshold, the system enters an alarm state, such as by sounding an audible alert. In another preferred embodiment, one or more thresholds are adjustable by the operator. Alternatively, the threshold can be calculated automatically by the system such as via an algorithm that uses distance D.

Distance D can be used in numerous algorithms of the system of the present invention, such as to modify, including initial creation of, a system parameter. System parameters include but are not limited to: a threshold parameter such as an increased temperature threshold; an alarm parameter such as an alarm "on" state; an energy parameter such as a parameter changing energy type or modifying energy delivery; a sensor parameter such as a parameter which activates one or more additional sensors; cooling apparatus parameter such as a parameter activating a cooling apparatus; and combinations thereof. In a preferred embodiment, the value of distance D is used in conjunction with a temperature reading, such as a temperature recorded on thermocouple 361, by a system algorithm to determine a system parameter value.

In an alternative embodiment, ablation catheter 100 and/or esophageal probe 300 include one or more integral sensors such as: an electrical signal sensor such as a cardiac electrode; a temperature sensor such as a thermocouple; an imaging transducer such as an array of ultrasound crystals; a pressure sensor; a pH sensor; a physiologic sensor such as a blood sensor, a respiratory sensor; an EEG sensor, a pulse oximetry sensor and a blood glucose sensor; an impedance sensor; a contact sensor; a strain gauge; an acoustic sensor; and combinations thereof. The information from these one or more sensors may be used by an algorithm of the system of the present invention, such as an algorithm processed by the interface unit providing energy to the ablation catheter.

Figure 3:
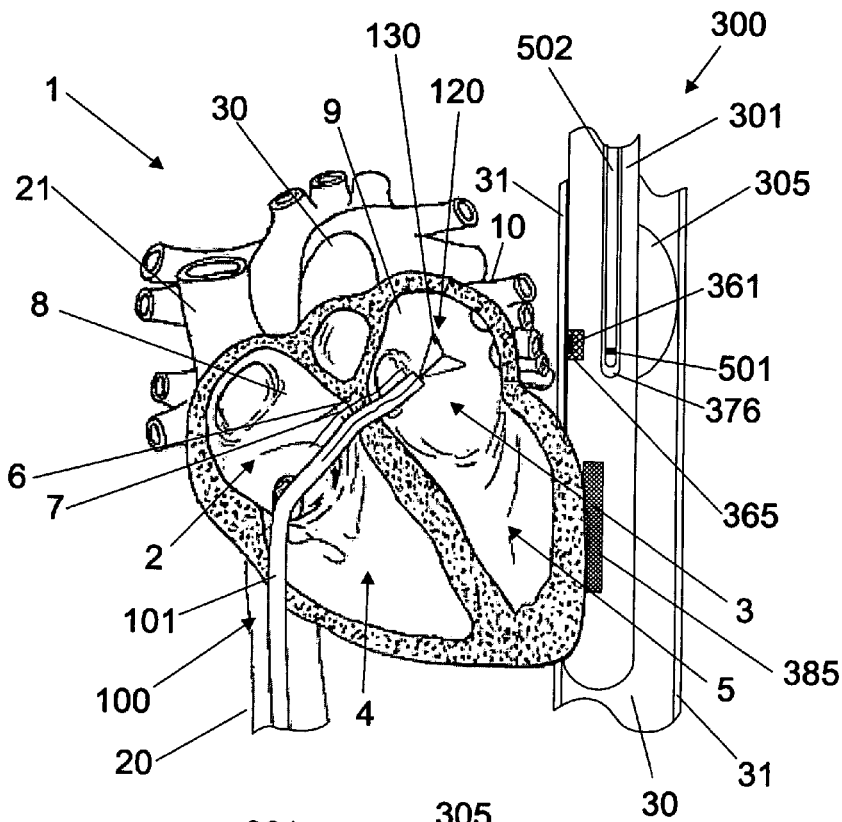
FIG. 3 illustrates another embodiment of the system of the present invention utilizing an ultrasound unit.

FIG. 3 illustrates an alternative embodiment of the present invention wherein an ablation catheter includes a location element integral to its structure and an esophageal probe includes a sealed, or blind lumen extending from its proximal end to near its distal end. An ultrasound probe or catheter is inserted into the blind lumen during the procedure and is used to determine the distance between its imaging element and the location element of the ablation catheter, the distance being used to determine one or more parameters of the system. FIG. 3 shows a cutaway view of the human heart 1 showing the major structures of the heart including right atrium 2, left atrium 3, right ventricle 4, left ventricle 5, atrial septum 6, fossa ovalis 7, atrial walls 8 and 9, as well as in the pulmonary veins 10 and the pulmonary arteries 11. Ablation of dysfunctional areas, referred to as arrhythmogenic foci (also referred to as drivers or rotors) as has been described hereabove, is an effective treatment for atrial fibrillation. The system of FIG. 3 provides means of creating lesions remote from the pulmonary veins and their ostia while being easily deployed to ablate the driver and rotor tissue without causing unnecessary tissue damage to the heart and neighboring tissues and structures such as the esophagus.

To accomplish the lesion creation, ablation catheter 100 is inserted into left atrium 3 as has been described in reference to FIG. 1. Catheter 100 may include an integral sheath, such as a tip deflecting sheath, or may work in combination with a separate sheath. Catheter 100 includes carrier assembly 120, a flexible structure with one or more ablation elements, such as heat generating RF electrodes, carrier assembly 120 extending beyond the distal end of catheter shaft 101 of catheter 100. Carrier assembly 120 is adapted to be deformable such that pressing carrier assembly into left atrial wall 9 will cause one or more and preferably all of electrodes 130 to make contact with the tissue to be analyzed and/or ablated. Each of the electrodes 130 is attached via connecting wires, not shown, that extend proximally and electrically attach to an interface unit of the system of the present invention. The interface unit of FIG. 3, RF delivery unit 200, provides at least RF energy to ablation catheter 100.

RF delivery unit 200 and ablation catheter 100 are configured to delivery one or more types of energy, in variable and/or modulated forms, and preferably also configured to provide electrical mapping of the tissue that is contacted by one or more electrodes integral to carrier assembly 120. Electrodes 130 can be configured to be mapping electrodes and/or additional mapping only electrodes can be integral to carrier assembly 120 to provide the cardiac signal mapping function. Carrier assembly 120 is configured to engage an endocardial surface to map and/or ablate tissue on the surface. In a preferred method, RF energy is delivered after a proper location of the electrodes 130 is confirmed with a mapping procedure. If the position is determined to be inadequate, carrier assembly 120 is repositioned through various manipulations performed at the proximal end of the ablation catheter 100 by an operator. In another preferred embodiment, RF delivery unit 200 is configured to accept a signal from one or more sensors integral to ablation catheter 100, not shown, such that the energy delivered can be modified via an algorithm which processes the information received from the one or more sensors.

The system of FIG. 3 further includes esophageal probe 300, inserted into esophagus 30 of the patient. Probe 300 is advanced to a location in relatively the closest available proximity to the cardiac tissue to be ablated, such as can be visualized and determined using fluoroscopy. Probe 300 includes a flexible shaft, shaft 301, which includes a temperature sensor, thermocouple 361, on the outer surface and near the distal end of shaft 301. Thermocouple 361 is covered by membrane 365, preferably a flexible structure such as an elastomeric membrane. Wires are connected to thermocouple 361 and extend proximally to the proximal end of probe 300, wires and proximal end not shown, such that the temperature at thermocouple 361 can be determined by signals transmitted to and/or from thermocouple 361 via the wires. The electronics necessary to transmit and/or receive the signals and determine the temperature may be integral to a handle, also not shown, on the proximal end of probe 300 and/or a separate device attached to a connector in electrical communication with the wires.

Esophageal probe 300 further includes balloon 305, such as a compliant or non-compliant balloon. Probe 300 includes an inflation port on its proximal end, and a lumen, both not shown, the lumen extending from the inflation port to the balloon such that balloon can be controllably inflated and deflated. Balloon 305 is located near the distal end of shaft 301 in close proximity to thermocouple 361 and radiopaque marker 331, such as at the same longitudinal position but eccentrically configured on the opposite side of shaft 301. In an alternative embodiment, balloon 305 is concentric with shaft 301. During the procedure, balloon 305 is rotationally oriented by torquing the proximal end of shaft 301. In a preferred method, balloon 305 is positioned such that when balloon 305 is inflated and contact between balloon 305 and esophageal wall 31 causes membrane 365 to contact the contralateral wall, thermocouple 361 is positioned in relatively the closest location within esophagus 30 to the intended heart tissue to be ablated.

At the distal end and on the outer surface of shaft 301 is securely mounted a functional element, electrode 385, which is connected to wires that extend to connection means at the proximal end of probe 300, wires and connection means not shown. Electrode 385, working in combination with one or more separate electrodes, such as an electrode on the ablation catheter 100 or an electrode placed on an exterior surface of the patient such as on the chest, can be used to transmit electrical energy between the two or more electrodes to perform a cardiac defibrillation procedure and/or a cardiac pacing procedure. When balloon 305 is inflated, electrode 385 contacts esophageal wall 31, on the contralateral wall from that contacted by balloon 305. Additionally or alternatively to probe 300, catheter 100 may include an electrode used to perform a cardiac defibrillation procedure and/or a cardiac pacing procedure. The electrical or other energy needed to perform such a cardiac defibrillation and/or cardiac pacing procedure can be provided the interface of the present invention, such as via a separate function of RF delivery unit 200. Each electrode utilized in a cardiac defibrillation and/or cardiac pacing procedure is preferably of sufficient surface area to prevent damage to tissue, such as electrode 385 being large enough to avoid damage to the esophagus of the patient. In a preferred embodiment, electrode 385 is positioned in the lower third of the patient's esophagus prior to performing a cardiac defibrillation or cardiac pacing procedure. Electrode 385 may have a dome-like geometry, such as a dome with a 0.7 inch radius of curvature. Alternatively or additionally, a ring-shaped electrode along a circumferential portion of catheter shaft 301, or catheter shaft 101, may be included.

Figure 4:
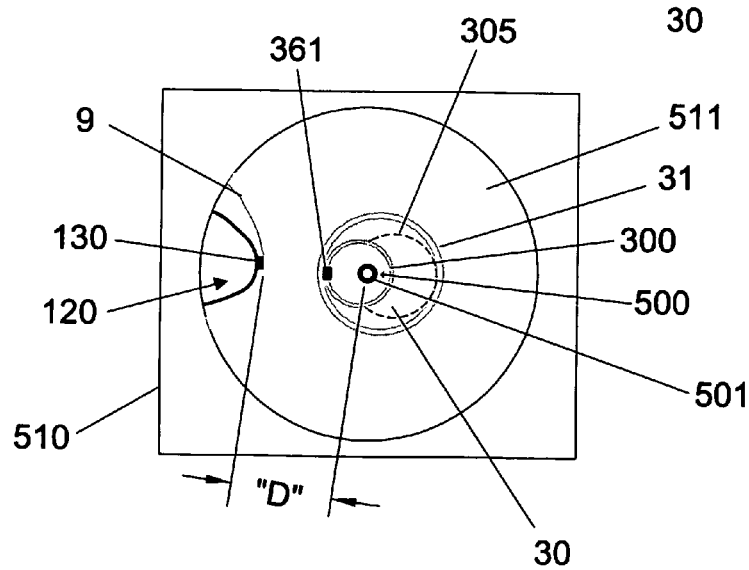
FIG. 4 illustrates the ultrasound monitor of the system of FIG. 3.

Insertion and positioning of ablation catheter 100 and esophageal probe 300 is performed under x-ray visualization as has been described in reference to FIG. 1 and FIG. 2. Probe 300 includes a lumen, blind lumen 376, which begins at an entry port on the proximal end of probe 300 and extends distally to a location near to the distal end of shaft 301 and terminates in a closed end that does not exit the interior portion of shaft 301 thus limiting the advancement of a catheter or other probe which is inserted into blind lumen 376. The system further comprises an ultrasound catheter including catheter shaft 502 with ultrasound crystal array 501 near its distal end. Ultrasound crystal array, such as an array of ninety-six crystals of similar construction to phased arrays of ultrasound crystals used in phased array intravascular ultrasound (IVUS) catheters, functions as a location element with a transmitter and receiver pair. Electrode 130 of catheter 100 is constructed of one or more materials that are ultrasonically reflective, such as a metal, such that electrode 130 functions as the location element of the ablation catheter. In alternative embodiments, another portion of catheter 100, preferably in close proximity to one or more electrodes 130, is ultrasonically reflective and performs as the location element of ablation catheter 100. Referring additionally to FIG. 4, array 501 transmits ultrasound signals in the plane extending radially outward from the circumference of the array. Crystals of array 501 also receive ultrasound signals that are reflected from all ultrasonically reflective surfaces, such that electrically connected ultrasound monitor 510 and display 511 can create and display a cross-sectional image of these reflective surfaces further providing radial distance information of these surfaces to array 501. In an alternative embodiment, the ultrasound catheter includes a rotating crystal or crystals to create the cross-sectional image, wherein a high speed rotating linkage is within a lumen of probe 300, and driven by a device external to the patient. In another alternative embodiment, the ultrasound crystal array is integral to shaft 301 of probe 300, such as an array mounted on or near the outer surface of shaft 301 in close proximity to thermocouple 361.

FIG. 4 depicts ultrasound monitor 510 with display 511 displaying an image of the cross-section of probe 300 and carrier assembly 120 of the ablation catheter, the cross-section defined by the plane of the circumference of ultrasound crystal array 501. Included in the cross-sectional image are the cross-section of ultrasound catheter 500, left atrial wall 9 and carrier assembly 120 including electrode 130. The distance D between ultrasound catheter 500 and electrode 130 can be manually calculated, such as by a person performing a measurement on screen 511, or automatically calculated such as via a software algorithm embedded in ultrasound monitor 510 or another component of the system of the present invention. Automatic distance calculating software can work with automatically identifiable cross-sectional profiles of the location elements, such as via pattern recognition algorithms, to automatically calculate the distance D between electrode 130 and ultrasound catheter 500. Since lumen 376 of shaft 301 is of pre-determined distance to thermocouple 361, the system can also determine the distance D' between thermocouple 361 and electrode 130 by subtracting from distance D. In addition to providing means for determining the distance D, the cross-sectional image provided on display 511 allows precise rotational orientation of the distal end of shaft 301, such as when balloon 305 is deflated or partially deflated. This precise and confirmed orientation can be used to position thermocouple 361 in the closest available proximity to electrode 130 of ablation catheter 100. FIG. 4 depicts the condition in which shaft 301 has been rotationally oriented and balloon 305 properly inflated such that thermocouple 361 is in the closest available proximity to electrode 130. In an alternative embodiment, either or both ablation catheter 100 and esophageal probe 300 include radiopaque markers such that fluoroscope can be used in addition to ultrasound imagery to rotationally and longitudinally position both ablation catheter 100 and esophageal probe 300 to optimize the ablation procedure and minimize non-therapeutic tissue damage.

Since tissue damage to the esophagus should be avoided, as well as damage to heart or other tissue that is not a cause of the patient's arrhythmia, the system of the present invention preferably uses a temperature threshold for the temperature detected via thermocouple 361 of esophageal probe 300. An algorithm for triggering a change to ablation energy, ablation "on" state, alarm state, or other system parameter compares the detected temperature to a temperature threshold. The threshold is preferably determined by distance D, such as via a look-up table of maximum temperatures versus distance, or an equation including those variables. This temperature threshold will be inversely proportional to the distance between thermocouple 361 and the electrodes of ablation catheter 100.

In a preferred embodiment, when the temperature sensed by thermocouple 361 reaches one or more pre-determined thresholds, the energy being delivered is modified. The modification can include changing the type or types of energy delivered such as from RF to microwave energies; changing the intensity of energy delivered including a stoppage of energy delivery; changing the frequency of energy delivered; changing a pulse width modulation parameter of energy delivered including changing monopolar and bipolar delivery on and off times; and combinations thereof. In another preferred embodiment, when the sensed temperature reaches a threshold, the system enters an alarm state, such as by sounding an audible alert. In another preferred embodiment, one or more thresholds are adjustable by the operator.

Distance D can be used in one or more other algorithms of the system of the present invention, such as to modify, including initial creation of, a system parameter. System parameters include but are not limited to: a threshold parameter such as an increased temperature threshold; an alarm parameter such as an alarm "on" state; an energy parameter such as a parameter changing energy type or modifying energy delivery; a sensor parameter such as a parameter which activates one or more additional sensors; cooling apparatus parameter such as a parameter activating a cooling apparatus; and combinations thereof.

Figure 5:
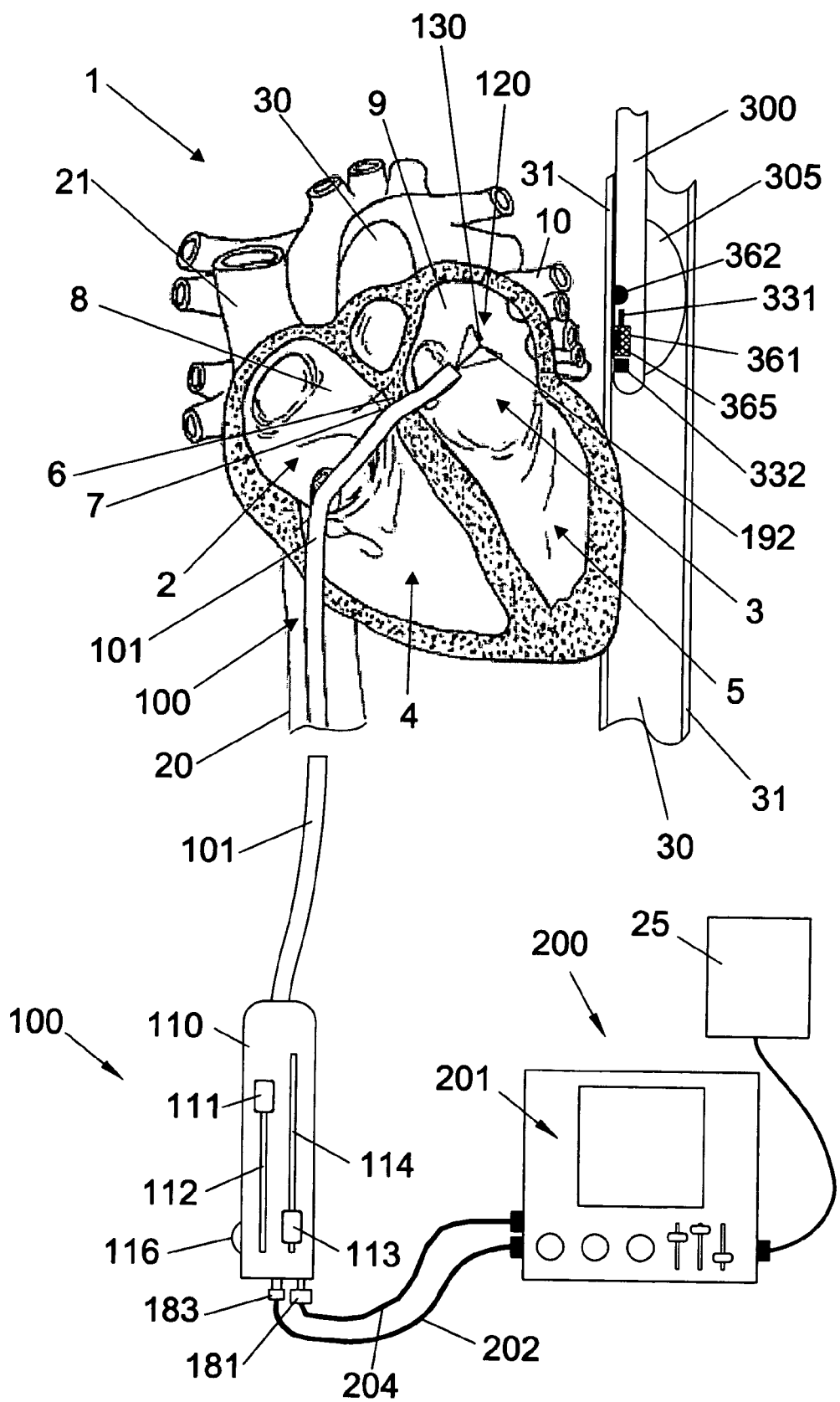
FIG. 5 illustrates another embodiment of the system of the present invention utilizing dual antennas.

FIG. 5 illustrates another alternative embodiment of the present invention wherein an ablation catheter includes a location element integral to its structure and an esophageal probe also includes a location element integral to its structure. One of the location elements includes a transmitter and the other location element includes a receiver for receiving one or more transmissions from the transmitter. The transmitter and receiver are used in conjunction to calculate the distance between a portion of a probe in the patient's esophagus and a portion of an ablation catheter in the heart of the patient. This calculated distance is used to determine a value for one or more parameters of the system. FIG. 5 shows a cutaway view of the human heart 1 showing the major structures of the heart including right atrium 2, left atrium 3, right ventricle 4, left ventricle 5, atrial septum 6, fossa ovalis 7, atrial walls 8 and 9, as well as in pulmonary veins 10 and pulmonary arteries 11. Ablation of dysfunctional areas, referred to as arrhythmogenic foci (also referred to as drivers or rotors) as has been described hereabove, is an effective treatment for atrial fibrillation. The system of FIG. 5 provides means of creating lesions remote from the pulmonary veins and their ostia while being easily deployed to ablate the driver and rotor tissue without causing unnecessary tissue damage to the heart and neighboring tissues and structures such as the esophagus.

To accomplish the lesion creation, ablation catheter 100 is inserted into left atrium 3 as has been described in reference to FIG. 1. Catheter shaft 101 is part of a steerable sheath, including a pull wire, not shown, which is secured at one end to the distal end of shaft 101 and at the other end is operably attached to knob 113, wherein knob 113 can be distally advanced or proximally retracted in slot 114. The pull wire is operably connected to the knob 113 so that sliding of knob 113 advances or retracts the pull wire to effectuate steering of the distal end shaft 101. Retraction of knob 113 proximally causes distal end of shaft 101 to deflect and advancement of knob 113 distally causes the distal end of shaft 101 to straighten. Using knob 113, the operator can steer the carrier assembly 120 as needed to contact different areas of the atrium wall or other tissue surface. In a preferred embodiment, knob 113 is operably connected to the pull wire via a cam, or set of gears, not shown, to provide a mechanical advantage in the distance traveled by the pull wire or the force transmitted to the pull wire.

Catheter 100 includes carrier assembly 120, a flexible structure with one or more ablation elements, such as heat generating RF electrodes 130. Carrier assembly 120 is shown extending beyond the distal end of catheter shaft 101 of catheter 100. Carrier assembly 120 is adapted to be deformable such that pressing carrier assembly into left atrial wall 9 will cause one or more and preferably all of electrodes 130 to make contact with the tissue to be analyzed and/or ablated. At the proximal end of ablation catheter 100 is a handle, handle 110. Handle 110 includes knob 111 that slides in slot 110. Knob 11 is attached, such as via a cam, to a control shaft which extends distally, through a lumen of shaft 101, and operably attaches to carrier assembly 120. Sliding of knob 111 toward the proximal end of catheter 100 causes carrier assembly 120 to retract and become radially constrained within the distal tip of shaft 101. Sliding of knob 111 toward the distal end of catheter 100 causes carrier assembly to advance outside of the distal end of catheter 100 and assume an expanded condition.

Each of the electrodes 130 of carrier assembly 120 is attached via connecting wires, not shown, that extend proximally and electrically attach to an interface unit of the system of the present invention. The interface unit of FIG. 5, RF delivery unit 200, provides RF energy to one or more ablation elements of ablation catheter 100. In alternative embodiments, different forms of energy, singly or in combination, can be supplied by the interface unit. RF delivery unit 200 and ablation catheter 100 are configured to delivery RF energy in monopolar, bipolar or combination monopolar-bipolar energy delivery modes. Patch electrode 25, preferably a conductive pad attached to the back of the patient, is used to deliver monopolar RF energy from electrodes 130. In a preferred embodiment, monopolar energy delivery is followed by bipolar energy delivery, which is then followed a period without energy delivery, such as a sequence in which the three steps have equal durations. In another preferred embodiment, RF delivery unit 200 is configured to also provide electrical mapping of the tissue that is contacted by one or more electrodes integral to carrier assembly 120. Electrodes 130 can be configured to be mapping electrodes and/or additional mapping only electrodes can be integral to carrier assembly 120 to provide the cardiac signal mapping function. Handle 110 includes button 116 that is configured to allow the operator to initiate delivery of energy to one or more ablation elements when button 116 is depressed.

Carrier assembly 120 is configured to engage an endocardial surface to map and/or ablate tissue on the surface. In a preferred method, RF energy is delivered after a proper location of the electrodes 130 is confirmed with a mapping procedure. If the position is determined to be inadequate, carrier assembly 120 is repositioned through various manipulations performed at the proximal end of the ablation catheter 100 by an operator. In another preferred embodiment, RF delivery unit 200 is configured to deliver both RF energy and ultrasound energy to the identical or different electrodes 130. In another preferred embodiment, RF delivery unit 200 is configured to accept a signal from one or more sensors integral to ablation catheter 100, sensors not shown, such that the energy delivered can be modified via an algorithm which processes the information received from the one or more sensors.

The system of FIG. 5 further includes esophageal probe 300, inserted into esophagus 30 of the patient. Probe 300 is advanced to a location in relatively the closest available proximity to the cardiac tissue to be ablated, such as can be visualized and determined using fluoroscopy. Probe 300 includes a flexible shaft, shaft 301, which includes a temperature sensor, thermocouple 361, on the outer surface and near the distal end of shaft 301. Thermocouple 361 is covered by membrane 365, preferably a flexible structure such as an elastomeric membrane. Wires are connected to thermocouple 361 and extend proximally to the proximal end of probe 300, wires and proximal end not shown, such that the temperature at thermocouple 361 can be determined by signals transmitted to and/or from thermocouple 361 via the wires. The electronics necessary to transmit and/or receive the signals and determine the temperature may be integral to a handle, also not shown, on the proximal end of probe 300 and/or be included in a separate device attached to a connector in electrical communication with the wires.

Esophageal probe 300 further includes balloon 305, such as a compliant or non-compliant balloon. Probe 300 includes an inflation port on its proximal end, and a lumen, both not shown, the lumen extending from the inflation port to the balloon such that balloon can be controllably inflated and deflated. Balloon 305 is located near the distal end of shaft 301 in close proximity to thermocouple 361 and radiopaque marker 331, such as at the same longitudinal position but eccentrically configured on the opposite side of shaft 301. In an alternative embodiment, balloon 305 is concentric with shaft 301, such as a concentric balloon with a thermal sensor on its outer surface. During the procedure, torquing the proximal end of shaft 301 can rotationally orient balloon 305. In a preferred method, balloon 305 is positioned such that when balloon 305 is inflated and contact between balloon 305 and esophageal wall 31 causes membrane 365 to contact the contralateral wall, thermocouple 361 is positioned in relatively the closest location within esophagus 30 to the intended heart tissue to be ablated. Probe shaft 301 further includes a sensor for determining adequate contact with the esophageal wall, contact sensor 362. Contact sensor 362 connects to one or more wires that extend proximally and are connected to electronics used to measure the level of contact. Contact sensor 362 may comprise a mechanical switch such as a collapsible dome switch, or a force sensing transducer such as a strain gauge. In a preferred embodiment, the temperature detected by thermocouple 361 is not used by the system unless an adequate level of contact is determined by signals received from contact sensor 362.

Insertion and positioning of ablation catheter 100 and esophageal probe 300 is performed under x-ray visualization as has been described in reference to FIG. 1 and FIG. 2. Probe 300 includes transmitting antenna 332, securely mounted in close proximity to thermocouple 36. In an alternative or additional embodiment, a receiving antenna is mounted to probe 300. In another alternative embodiment, an antenna is mounted to a catheter or probe which is inserted into a lumen of probe 300, such that the antenna can be slidingly received and removed from probe 300, and/or movably positioned within probe 300. Working in conjunction with transmitting antenna 332 is receiving antenna 192 securely mounted to ablation catheter 100, preferably near one or more electrodes 130. In an alternative or additional embodiment, a transmitting antenna is mounted to catheter 100. In another alternative embodiment, an antenna is mounted to a catheter or probe that is inserted into a lumen of catheter 100, such that the antenna can be slidingly received and removed from catheter 100, and/or movably positioned within catheter 100.

Transmitting antenna 332 and receiving antenna 192 function as location elements of esophageal probe 300 and ablation catheter 100 respectively. In a preferred embodiment, transmitting antenna 332 is configured to transmit sound waves that are received by receiving antenna 192. The system calculates the distance between the two location elements based on the speed of that particular sound in tissue, and the time duration between the initial transmission of the sound and the initial receipt of that sound. Specific sound patterns can be used to confirm or enhance the time duration measurement.

The interface of FIG. 5, RF delivery unit 200 includes user interface 201 which includes an information screen and other components. Delivery unit 200 is attached via cable 204 to functional element attachment port 183 of catheter 100. Delivery unit 200 is attached via cable 202 to RF attachment port 181 of catheter 100. Functional element attachment port 183 provides electrical connection to receiving antenna 192, as well as one or more other components or sensors such as mapping electrodes, temperature sensors and other antennas. Additional ports and additional cables can be included in delivery unit 200, these cable comprising electrical wires, optical fibers, tubular conduits and/or other filamentous elongate structures. Delivery unit 200 is preferably connected to esophageal probe 300, cable and connection not shown, such that signals and energy can be delivered to or received from one or more functional elements of esophageal probe 300 such as thermocouple 361, transmitting antenna 332 and other transmitters or sensors not shown. User interface 201 includes user input devices such as buttons and touch screens, and user output components such as video screens, alphanumeric displays and audible transducers. The value of one or more system parameters can be viewed, set or calculated via user interface 201, including values for energy delivery parameters, temperature readings, temperature thresholds, and other system parameters.

Delivery unit 200 sends signals to transmitting antenna 332 of probe 300 and receives signals from receiving antenna 192 of catheter 100 such that the time between initiating transmission of sound signals from antenna 332 to receiving initial transmission of sound signals from antenna 192 can be measured. The measurement value is used to calculate the distance between the two antennas, based on the speed of sound in the relevant tissue. In alternative embodiments, other forms of signals, such as electromagnetic waves, can be transmitted and received such that measurement of one or more properties, such as signal amplitude or phase, can be utilized to calculate the distance between the two antennas. Since transmitting antenna 332 of shaft 301 is of a pre-determined distance to thermocouple 361, the system can also determine a second distance value, the distance between thermocouple 361 and electrode 130 by subtracting from the first distance value. In a preferred method, probe 300 is longitudinally and rotationally oriented under fluoroscopy, X-ray unit not shown, to position thermocouple 361 in the closest available proximity to electrode 130 of ablation catheter 100.

Since tissue damage to the esophagus should be avoided, as well as damage to heart or other tissue that is not a cause of the patient's arrhythmia, the system of the present invention preferably uses a temperature threshold for the temperature detected via thermocouple 361 of esophageal probe 300. An algorithm for triggering a change to ablation energy, ablation "on" state, alarm state, or other system parameter compares the detected temperature to a temperature threshold. The threshold is preferably determined by a first distance between the location elements, or a second distance based on the first distance, such as via a look-up table of maximum temperatures versus distance, or an equation including those variables. This temperature threshold will be inversely proportional to the distance between thermocouple 361 and the electrodes of ablation catheter 100. When the temperature sensed by thermocouple 361 reaches one or more pre-determined thresholds, the energy being delivered can be modified, and/or one or more other system parameters can change value or state, as has been described in detail hereabove. The temperature thresholds are based on the distance calculated by the system of the present invention. One or more additional sensors, integral to ablation catheter 100 or esophageal probe 300 may provide signal information which is also used by one or more algorithms of the system, such as in conjunction with the calculated distance, to initiate or change a value of a system parameter.

In an alternative embodiment, alternative or in addition to any transmitting or receiving antennas of esophageal probe 300 or ablation catheter 100, additional transmitting antennas and/or receiving antennas can be placed within the body of the patient, or on the patient's skin, such as on the patient's chest. These configurations, including three or more antennas, can be used to determine the distance between a portion of probe 300 and a portion of catheter 100, using antenna based positioning techniques including Doppler positioning techniques and triangulation positioning methods. Transmitted signals, such as electromagnetic signals, sound signals, light signals and other tissue penetrating signals can be sent from one or more transmitting antennas, to one or more receiving antennas. In a preferred embodiment, one or more antennas is configured to both transmit and receive signals. The signals transmitted and received in these embodiments are used by the calculating means of the present invention to determine the distance between two or more location elements of the system. The calculating means are preferably integral to the interface unit of the present invention. The interface unit utilizes one or more algorithms that perform one or more signal processing techniques to analyze electromagnetic wave properties; signal amplitude properties; signal phase angle and frequency properties; and combinations thereof. Antennas may include conductive plates such as parabolic plates, multiple turn coils, or other transmitting or receiving structures.

In another preferred embodiment, the esophageal probe includes two transmitting antennas, such as two or more coils separated by a distance, and the ablation catheter includes a receiving antenna. Each of the coils is configured to transmit an electromagnetic signal at a different frequency from the other, such as frequencies of 20 KHz and 40 KHz. The ablation catheter receiving antenna picks up these signals, and the calculating means of the system utilizes the relative signal strength to determine the position of the receiving antenna in relation to the two transmitting coils. In an alternative embodiment, the ablation catheter includes the two transmitting antennas that transmit electromagnetic signals of different frequencies and the esophageal probe includes the receiving antenna which receives the two signals, the receipt of which is used by the calculating means to determine the relative position of the esophageal probe to the ablation catheter.

Figure 6:
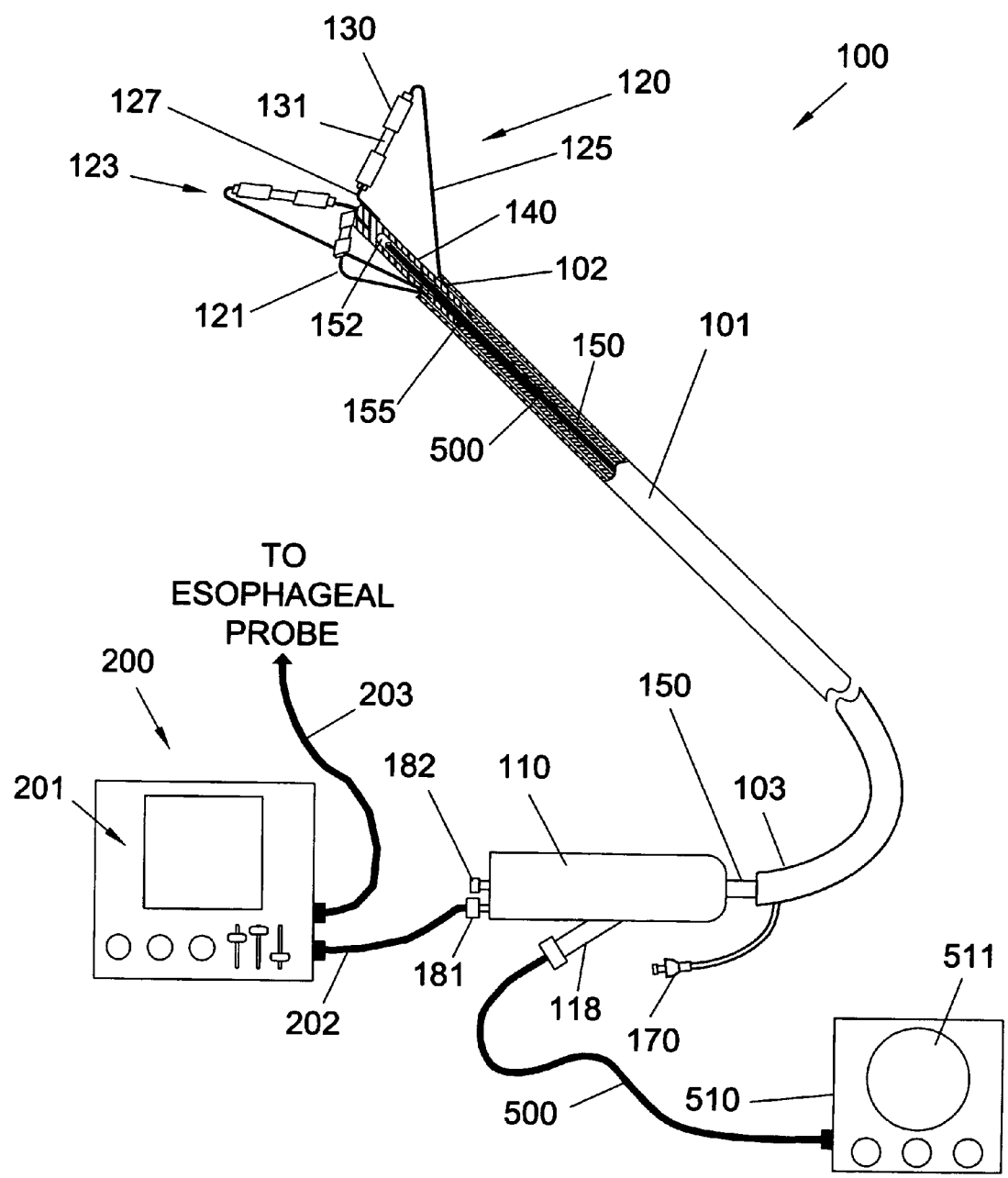
FIG. 6 illustrates a perspective, partial cutaway view of a preferred embodiment of an ablation catheter consistent with the present invention in which the carrier element has three carrier arms, the ablation catheter further including a blind lumen with an IVUS catheter in place.

Referring now to FIG. 6, a preferred embodiment of an ablation catheter of the present invention is illustrated wherein the ablation catheter comprises a sheath with a removable core, the core including a carrier assembly with electrodes as well as a lumen for insertion of an intravascular ultrasound (IVUS) catheter that functions as a location element of the ablation catheter. As shown in FIG. 6, ablation catheter 100 includes a tubular body member that is an elongate, flexible, hollow tube, catheter shaft 101. The material used for the construction of the catheter shaft 101 and each component which resides or is configured to be inserted through a lumen integral to catheter shaft 101, are selected to provide the suitable flexibility, column strength and steerability to allow percutaneous introduction of ablation catheter 100 to various body locations including the left or right atrium of the heart. Catheter shaft 101 and other tubular conduits of ablation catheter 100 are constructed of materials such as Pebax™; polyimide; polyurethane; silicone; nylon; polyvinyl chloride (PVC); polyester; and combinations thereof. These types of conduits may be constructed of an outer layer, an inner layer and a braid residing therebetween. The braid may be constructed of various materials including stainless steel; Nitinol; monofilament fiber; a polymer; and combinations thereof.

Control shaft 150 enters and extends from the proximal end to distal end 102 of catheter shaft 101 and slidingly resides in a lumen therebetween such that control shaft 150 and distally connected components can be completely removed from catheter shaft 101. Control shaft 150 is also constructed of materials that provide suitable flexibility and column strength to be percutaneously introduced into the patient as well as perform other functions such as the advancement and contraction of carrier assembly 120. Applicable materials for control shaft 150 are Nitinol; stainless steel; titanium; gold; platinum; copper; a polymer; a polymer embedded with conductive material; an elastomer; a plastic; and combinations thereof. In a preferred embodiment, control shaft 150 is constructed of both stainless steel and Nitinol. In another preferred embodiment, control shaft 150 is selected from the group consisting of: a monofilament fiber; a spring coil; a wire; and combinations thereof. In another preferred embodiment, control shaft 150 has a guidewire construction such as a core with a tightly coiled wire sheath, the sheath surrounding a substantial length of the core. In another preferred embodiment, the control shaft 150 includes a thru lumen extending from its proximal end to its distal end such as to permit over-the-wire introduction via that lumen.

Catheter shaft 101 is preferably part of a steerable sheath, steering mechanism not shown, and includes flush port 170, which is configured to be attachable to a flushing syringe, used to flush blood and other debris or contaminants from the lumen of an empty catheter shaft 101 (wherein control shaft 150, coupler 140 and carrier assembly 120 have been removed) or for flushing the space between control shaft 150 and the inner wall of catheter shaft 101. Catheter shaft 101 is not connected to handle 110, such that handle 110 can be withdrawn, removing control shaft 150, coupler 140 and carrier assembly 120 from catheter shaft 101. This configuration is useful when these components are provided in a kit form, including combinations of different versions of these components, the different combinations made available to treat multiple patients, or a single patient requiring multiple electrode patterns. A preferred example of a kit would include the catheter shaft 101 and flush port 170 of FIG. 6 acting as a sheath; kitted with handle 110, control shaft 150, coupler 140 and umbrella tipped carrier assembly 120 of FIG. 6 as well as a handle, control shaft, coupler and different shaped carrier assembly.

Carrier assembly 120 can be configured to assume numerous geometries when in its expanded as well as constrained conditions. Expanded geometries include but are not limited to: the umbrella configuration of FIGS. 1, 3, 5 and 6; a spiral shaped geometry; and other geometries. Carrier assembly 120, coupler 140 and control shaft 150 are configured such that control shaft 150 can be retracted to constrain carrier assembly 120 within a lumen of catheter shaft 101 and advancement of control shaft 150 causes carrier assembly 120 to advance beyond distal end 102 of control shaft 101 thus allowing carrier assembly 120 to deploy to its fully expanded condition. An operator of the system can, with minimal effort, advance handle 110 forward while holding proximal end 103 of shaft 101 in a relatively fixed position, causing carrier assembly 120 to advance to its distal position where it is fully deployed for engagement with tissue. Handle 110 can subsequently be retracted, also while holding proximal end 103 of shaft 101 in a relatively fixed position, to cause carrier assembly 120 to retract and be constrained within the distal end 102 of catheter shaft 101.

Coupler 140, located at the distal end of control shaft 150, connects control shaft 150 to carrier assembly 120. Coupler 140 may include a groove or longitudinal projection, both not shown, which mates with a corresponding projection or groove within the lumen of catheter shaft 101, such mating geometries used to prevent rotation of control shaft 150. Carrier assembly 120 is a flexible multi-filament assembly that includes at least one ablation element, such as electrode 130, to deliver energy to tissue. Carrier assembly 120 of FIG. 6 includes three carrier arms 123, each of which has a proximal arm segment 125 and a distal arm segment 127, which are connected by a resiliently flexible segment, carrier arm bend portion 121. One end of each distal arm segment 127 is attached to coupler 140. The ends of the distal arm segments 127 and the ends of the proximal arm segments 125 can be attached to the outside of coupler 140, the inside of coupler 140 or both. Bend portion 121 may include various elements to assist in bending such as a spring; a hinge; a reduced diameter segment; a bend created during a heat treatment of a wire such as the "training" of a Nitinol wire; and combinations thereof. Bend point 121 provides means for rotatably and flexibly joining a distal arm segment 127 to a proximal arm segment 125.

Control shaft 150 includes a sealed lumen, blind lumen 152, which extends into coupler 140, such that a catheter can be inserted within control shaft 150 and coupler 140 to a location within the expanded portion of carrier assembly 120. Coupler 140 is attached to control shaft 150 via joint 155 that provides a continuous opening of lumen 152 from control shaft 150 to coupler 140. Intravascular ultrasound (IVUS) catheter 500 is inserted through IVUS port 182 of handle 110, into lumen 152 and advanced to a distal location such that a cross-sectional image within carrier assembly 120 can be visualized, as well as images of neighboring structures, such as the atrial walls of the heart, and neighboring devices, such as the esophageal probe of the present invention when the probe is placed in a portion of the esophagus in relative proximity to the portion of tissue to be ablated.

In an alternative embodiment, an additional lumen, a thru lumen extending from the proximal end to the distal end of catheter 100 can be used for over-the-wire delivery, such as a trans-septal wire placed as described in reference to FIG. 1. In another alternative embodiment, lumen 152 is a thru lumen that extends to and exits the distal end of coupler 140 such that catheter 100 can be inserted over a trans-septal guidewire, the end of the guidewire exiting IVUS port 118. IVUS catheter 500 can be then introduced over the wire, also through port 118. In an alternative embodiment, the guidewire is removed prior to inserting IVUS catheter 500. Referring back to FIG. 6, IVUS catheter 500 is attached to IVUS monitor 510 that is a part of the interface unit of the present invention, and includes IVUS display 511. The cross-sectional image displayed on display 511 is used to calculate the distance between the central lumen of coupler 140 and a location element of an esophageal probe of the present invention, said probe located within the esophagus of the patient. This calculated distance, calculated automatically, manually or combinations of both, is used to determine one or more system parameter values, as is described throughout this application.

Carrier arms 123 are preferably constructed of a wire, such as a ribbon wire, and may have segments with different levels of flexibility. In a preferred embodiment, proximal arm segment 125, distal arm segment 127 and bend portion 121 are a continuous, resiliently flexible, trained Nitinol wire. Alternatively, bend point 121 may comprises two or more wires bonded together with a joint. The carrier arms 123 of FIG. 6 extend radially out from the central axis of distal end 102 of catheter shaft 101 and each carrier arm 123 includes two electrodes 130. In alternative embodiments, different patterns of electrodes, and different numbers or shapes of carrier arms are employed. In other alternative embodiments, carrier arms may be void of any ablation elements, such as a carrier arm to provide support only; and carrier arms may include, with or without the inclusion of ablation elements: mapping electrodes; thermal sensors or other sensors; transducers; and antennas, radiopaque markers or other location elements. In a preferred embodiment, each carrier arm 123 includes at least one ablation element. In another preferred embodiment, one or more ablation elements are radiopaque.

Referring back to FIG. 6, each electrode 130 is mounted to an insulator, insulating band 131 such that the electrode is electrically isolated from the wire segments of carrier assembly 120. In an alternative embodiment, each carrier arm is an insulated wire, and each electrode mounted to the insulating material. Each electrode 130 is connected to wires, not shown, that extend in parallel to, and are fixedly attached to, the shafts of carrier assembly 120. These wires include insulation to electrically isolate one wire from another. The materials and geometries of construction for the wires and their insulators are chosen to support the current and voltages required to complete the procedure. The wires may pass through coupler 140, along side coupler 140, or may be electrically connected to coupler 140 such that these wires connect to wires on the proximal end of coupler 140. The wires extend proximally to handle 110, and each wire may be within a lumen internal to control shaft 150, within the walls of control shaft 150, or fixed to the external wall of control shaft 150. The wires are electrically connected to attachment port 181 of handle 110. Additional wires or other flexible conduits, connected to one or more transducers, sensors or other functional elements, integral to carrier assembly 120, can be configured along a similar path to the electrode 130 wires, and can attach to port 181 or a separate port, not shown.

The electrodes 130 are provided a single drive signal or two or more alternating drive signals. Return or ground signals are provided by a separate electrode internal to the patient, or a skin electrode such as a patch electrode placed on the patient's back as is described in FIGS. 1 and 3. Electrodes 130 can be wired independently, such that each electrode 130 can deliver energy independent of any other electrode, or two or more electrodes can be connected in parallel or serial fashion. Also depicted in FIG. 6 is RF delivery unit 200, an interface unit of the present invention that connects to handle 110 with multi-conductor cable 202 at attachment port 181. In a preferred embodiment, ablation catheter 100 and delivery apparatus 200 are configured to drive two or more ablation elements, such as electrodes 130, independently or simultaneously. In an alternative embodiment, an energy delivery apparatus is integrated into handle 110 such that a separate apparatus and port 181 are not needed. In this configuration, handle 110 may include a plug, not shown, for attachment to a power supply or wall outlet. In another alternative embodiment, handle 110 includes an audible transducer, such as an audible transducer that is activated when energy is being delivered to tissue, or an alarm condition has been entered. In another alternative embodiment, handle 110 includes a power supply, such as a battery or rechargeable battery, both not shown. In another alternative embodiment, ablation catheter 100 includes one or more elements requiring power such as from an integrated battery, these elements selected from the group consisting of: an integral light such as an LED; a display such as a liquid crystal display or touch screen display; an audible transducer; a tactile transducer such as a vibration transducer which readily alerts anyone holding the device; a relay such as a relay which disconnects power to one or more ablation elements; mapping circuitry embedded in one or more components of ablation catheter 100, or electrode 130; and combinations thereof.

Referring back to FIG. 6, RF delivery unit 200 includes user interface 201, such as a user interface including data input devices like touch screens, buttons, switches, keypads, magnetic readers and other input devices; and also including data output devices like screens, lights, audible transducers, tactile transducers and other output devices. User interface 201 is used to select one or more electrodes to receive energy, set power levels, durations, threshold levels and other ablation and other system parameters, initiate power delivery, enter distance information, calculate distance information, deactivate an alarm condition and other functions common to electronic medical devices. In a preferred embodiment, RF delivery unit 200 also includes cardiac mapping means, such that mapping attachment port 182 can be attached to RF delivery unit 200 avoiding the need for a separate piece of equipment in the system. In another preferred embodiment, RF delivery unit 200 can also deliver ultrasound and/or another form of energy, such energy delivered by one or more additional ablation elements integral to carrier assembly 120, additional ablation elements not shown. Applicable types of energy include but are not limited to: sound energy such as acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof.

Referring back to FIG. 6, delivery unit 200 includes cable 203 that is attached to an esophageal probe of the present invention, esophageal probe not shown. Delivery unit 200 can send or receive signals to or from one or more functional elements, such as sensors and transducers, of the esophageal probe. Delivery unit 200 can also send or receive power to or from one or more functional elements, such as a pacing electrode or a defibrillation electrode of the esophageal probe.

In a preferred embodiment, ablation catheter 100 includes an embedded identifier (ID), an uploadable electronic or other code, which can be used by RF delivery unit 200 to confirm compatibility and other acceptability of the specific catheter 100 with the specific RF delivery unit 200. The electronic code can be a bar code, not shown, on handle 110 which is read by RF delivery unit 200, an electronic code which is transferred to RF delivery unit 200 via a wired or wireless connection, not shown, or other identifying means, such as an RF tag embedded in handle 110. In another preferred embodiment, RF delivery unit 200 also includes an embedded ID, such as an ID that can be downloaded to catheter 100 for a second or alternative acceptability check. The embedded ID can also be used to automatically set certain parameters or certain parameter ranges, and can be used to increase safety by preventing inadvertent settings outside of an acceptable range for the specific catheter 100.

Figure 7:
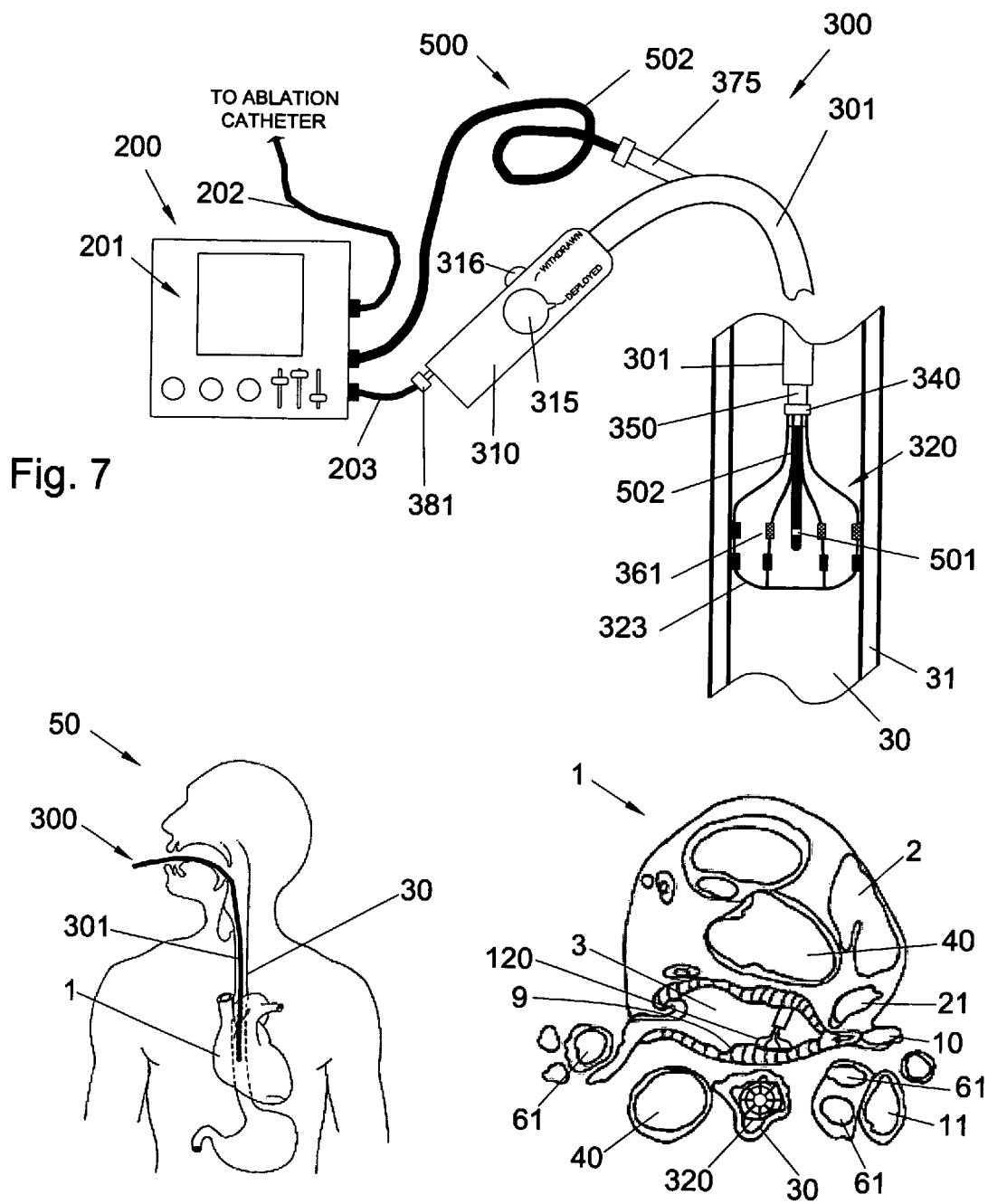
FIG. 7 illustrates a perspective, partial cutaway view of a preferred embodiment of an esophageal probe consistent with the present invention in which the probe includes a deployable, cylindrical carrier element including multiple sensors, the esophageal probe further including a thru lumen with an IVUS catheter extending beyond the distal end.

Referring now to FIG. 7, an esophageal probe and interface unit of the present invention are illustrated. The esophageal probe includes an insertable IVUS catheter that functions as a location element and a deployable carrier assembly that includes multiple sensors and/or transducers. Probe 300 includes shaft 301 that includes IVUS port 375 on its proximal end. Control shaft 350 is slidingly received with a lumen of shaft 301 and connects to carrier assembly 320 via coupler 340. At its proximal end, control shaft 350 is operably attached to knob 315 of handle 310 such that rotation of knob 315 can retract carrier assembly 320 to a constrained state within a lumen of shaft 301 and the reverse rotation of knob 315 causes carrier assembly 320 to advance distal to the lumen to an expanded state. Advancement and retraction of carrier assembly 320 of esophageal probe 300 is accomplished in similar fashion to the advancement and retraction of the carrier assembly of the ablation catheter of FIG. 6. In an alternative embodiment, probe 300 further includes deflecting means, such as has been described in reference to the ablation catheter of FIG. 5. These deflecting means, such as an eccentric inflatable balloon or controllable pull wire, can be used to cause the distal end of shaft 301, including one or more components mounted to the distal end, to make contact with esophageal wall 31.

Carrier assembly 320 is shown in its expanded state wherein carrier arms 323 make contact with esophageal wall 31 of esophagus 30. Carrier assembly 320 includes multiple thermocouples 361 securely mounted on carrier arms 323 such that when carrier assembly 320 is expanded, one or more thermocouples 361 make contact with esophageal wall 31. Extending from a lumen of control shaft 350 and coupler 340 is IVUS catheter shaft 502 that includes ultrasound crystal array 501. Array 501, preferably a fixed array of ultrasound crystals, sends and receives signals which are used to produce a cross-sectional image of the plane extending radially outward from the circumference of array 501. In a preferred embodiment, carrier arms 323 include one or more additional functional elements such as sensors or transducers to produce, receive and/or transmit signals or power as has been described in detail hereabove. Each sensor and/or transmitter, including thermocouples 361 are attached to wires, not shown, that extend proximally and connect one or more devices external to the patient.

IVUS catheter 500 enters IVUS port 375 at the proximal end of catheter shaft 301. IVUS catheter 500 is shown attached to RF delivery unit 200, which includes user interface 201. Interface 201 is configured to display the cross-sectional image produced by array 501 of IVUS catheter 500. Delivery unit 200 further includes cable 202 which attaches to the ablation catheter of the present invention, ablation catheter not shown. Delivery unit 200 attaches to esophageal probe 300 via cable 203 at attachment port 381. Cable 203 includes electrical conduits, fiber optic cables and/or other signal transmission filaments that attach to the functional elements of probe 300 including but not limited to, thermocouples 361. Handle 310 includes button 316 which is used to activate the transmission of energy to one or more transducers mounted on carrier arms 323 of carrier assembly 320, transducer not shown but preferably an electrode used to transmit or receive electrical signals that modify the cardiac function of the patient.

Referring now to FIG. 7a, the means of entry of the esophageal probe of the present invention is illustrated. Esophageal probe 300 is shown entering the mouth of patient 50, with shaft 301 advanced into a portion of esophagus 30 such that a distal portion of shaft 301 is in close proximity to cardiac tissue of heart 1. Referring now to FIG. 7b, a cross sectional image of a heart 1, esophagus 30 and neighboring tissue and vessels is illustrated. Also displayed are cross-sectional images of right atrium 2, left atrium 3 including left atrial wall 9, pulmonary vein 10, pulmonary artery 11, superior vena cava 21, aorta 40 and bronchus 61. Carrier assembly 120 of the ablation catheter of the present invention is shown pressed into wall 9 of left atria 3, such that electrodes included on its carrier arms make contact with targeted tissue to be ablated. Within esophagus 30 is the esophageal probe of the present invention, including expandable carrier assembly 320, similar to the carrier assembly of FIG. 7, carrier assembly 320 including multiple sensors or transducers, such as multiple thermocouples. In a preferred embodiment, the temperature at each of multiple sensors is determined, and the maximum temperature is used to compare to a threshold, as has been described in detail hereabove working in conjunction with a calculated distance between one or more components of esophageal probe 300 and ablation catheter 100.

Figure 8:
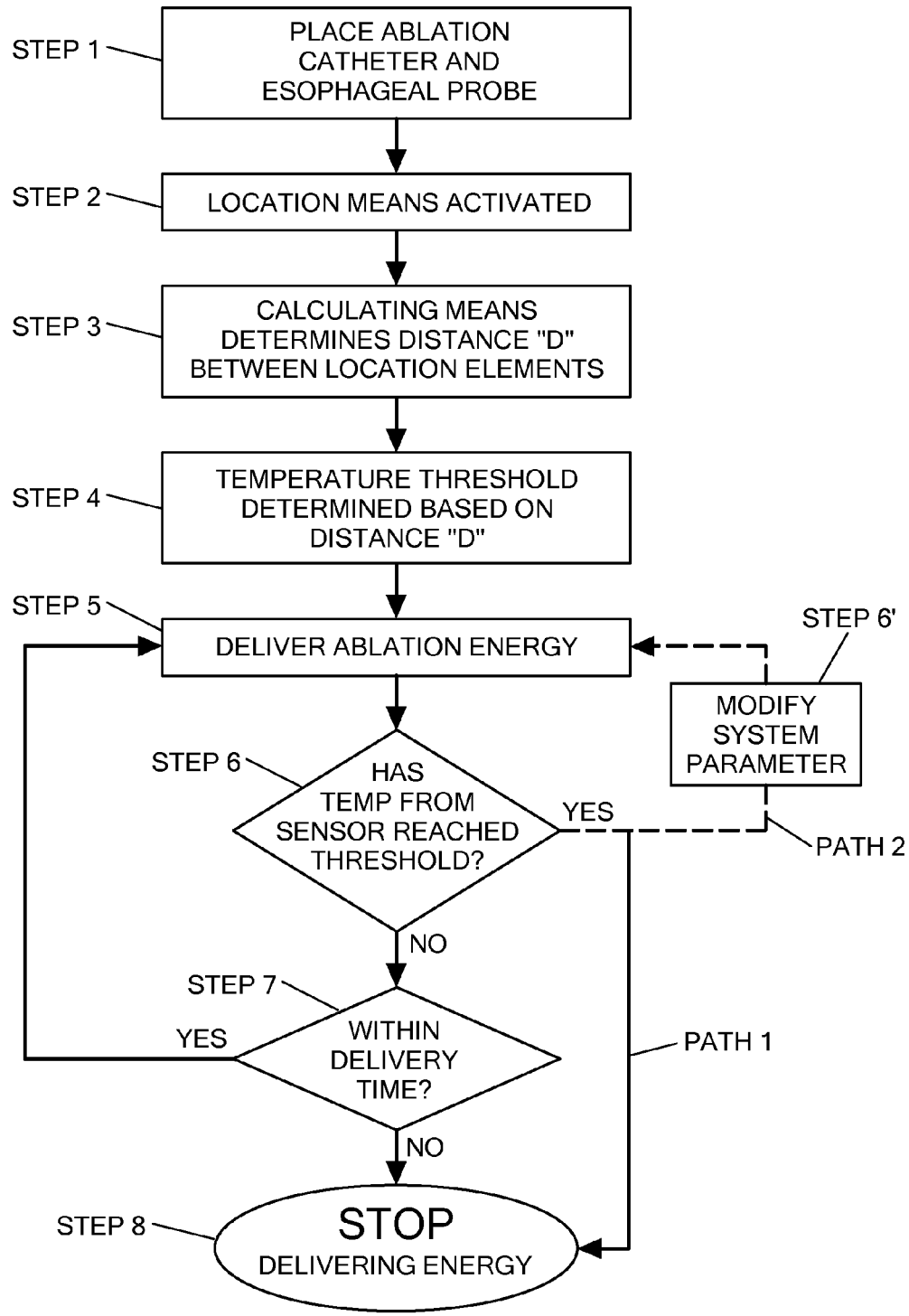
FIG. 8 illustrates a flow chart of a preferred step-wise configuration of the system of the present invention.

Referring now to FIG. 8, a preferred embodiment of the step-wise configuration of the systems and methods of the present invention is illustrated. STEP 1 represents an initial step including the placing of the ablation catheter into the heart and the esophageal probe into the esophagus as has been described in detail hereabove. STEP 2 represents the next sequential step including the activation of the location means of either or both the ablation catheter and the esophageal probe. Activation may include applying or receiving power, sending or receiving one or more signals, or otherwise activating one or more location elements to cause a signal to be detected and measured to determine the distance between a location element integral to the ablation catheter and a location element integral to the esophageal probe. STEP 3 represents the next sequential step including the calculation of the distance by the calculating means of the system of the present invention. As has been described hereabove, the calculating means may involve mechanical measurements or calculations made by a person, such as reading a distance off of an ultrasound or fluoroscopy monitor. Alternatively or additionally, the calculating process may be performed automatically, in part or in full, by one or more components of the system such as the interface unit that provides energy to the ablation catheter.

STEP 4 is the next sequential step including the calculation of a temperature threshold wherein the algorithm used to calculate the temperature threshold includes or is otherwise impacted by the value of the calculated distance between the location element of the ablation catheter and the location element of the esophageal probe. STEP 5 is the next sequential step including the delivery of ablation energy, provided by the interface unit, by one or more ablation elements of the ablation catheter. As STEP 5 is occurring, the delivery of energy to tissue, STEP 6 is initiated including reading signals from one or more sensors, such as thermocouples, that are integral to the esophageal probe. The signals correspond to the temperature at the associated sensor. In configurations wherein multiple temperature sensors are used, a preferred embodiment utilizes the calculated temperature that is the maximum temperature recorded. Also included in STEP 6 is the comparison of the appropriate temperature to the threshold calculated in STEP 4. Depending on the results of that comparison, different sequential steps will occur. If the temperature is beneath the threshold, STEP 7 is initiated which determines if the elapsed time since energy delivery initiation meets or exceeds a pre-determined delivery time. If the elapsed time is under the intended delivery time, the process returns to STEP 5 and subsequent steps repeat. If the elapsed time is at or greater then the intended delivery time, STEP 8 is initiated, STEP 8 including the stoppage of energy delivery.

Referring back to STEP 6, if the temperature detected has reached or exceeds the calculated threshold of STEP 4, STEP 7 is not initiated. Instead, in a preferred embodiment, PATH 1 is followed wherein STEP 8 is the next sequential step and the energy delivered is ceased. In another preferred embodiment, PATH 2 is followed wherein an additional step, STEP 6' is initiated. STEP 6 involves the modification of a system parameter, including but not limited to: the path of energy delivery changing from monopolar delivery to bipolar delivery, the level of energy delivery such as a decrease in amplitude of the energy delivered, a change in the form of energy delivered such as changing from RF energy to laser and/or ultrasound energy; the activation of an audible transducer alerting the operator the threshold has been reached; the entering of an alarm state of the system; the initiation of a cooling procedure such as a cool saline flush cooling procedure wherein cooled saline is introduced in the area surrounding the tissue being ablated; the changing of the threshold to a higher level such as when the operator is alerted that the first threshold has been met or exceeded; and combinations thereof. PATH 2 which includes STEP 6' further moves back to STEP 5 where energy continues to be delivered and the subsequent steps repeat.

It should be understood that numerous other configurations of the systems, devices and methods described herein may be employed without departing from the spirit or scope of this application. The system includes multiple functional components, such as the ablation catheter, the esophageal probe, and the interface unit. The interface unit preferably includes at least a portion of the calculating means for determining the distance between a location element in the esophageal probe and a location element in the ablation catheter. The ablation catheter includes at least one ablation element for delivering energy to cardiac tissue. Cardiac tissue applicable for ablation includes left and right atrial walls, as well as other tissues including the septum and ventricular tissue. The distance determined by the calculating means can be used to modify one or more system parameters, such as a temperature threshold for a temperature measured by a sensor in the esophageal probe.

The ablation catheter and esophageal probe of the present invention both include a flexible shaft with a proximal end, a distal end, an exterior wall and a location element. The flexible shafts may include one or more lumens, such as thru lumens or blind lumens. A thru lumen may be configured to allow over-the-wire delivery of the catheter or probe. Alternatively the catheter may include a rapid exchange sidecar at or near its distal end, consisting of a small projection with a guidewire lumen therethrough. A lumen may be used to slidingly receive a control shaft with a carrier assembly on its distal end, the carrier assembly deployable to exit either the distal end or a side hole of the flexible shaft. The advancement of the carrier assembly, such as through a side hole, via controls on the proximal end of the device, allows specific displacement of any functional elements, such as electrodes, mounted on the carrier assembly. Other shafts may be incorporated which act as a rotational linkage as well as shafts that retract, advance or rotate one or more components. The lumen may terminate in a side hole wherein the side hole functions as a suction port, such as a suction port that is used to maintain a portion of the exterior wall of flexible shaft of the esophageal probe against the wall of the esophagus. A lumen may be used as an inflation lumen, which permits a balloon mounted on a portion of the exterior wall of the flexible shaft to be controllable inflated and deflated. The balloon may be concentric or eccentric with the central axis of the shaft, it may be a perfusion balloon, and may include an in-line pressure sensor to avoid over-pressurizing a luminal structure such as the esophageal wall. A lumen may be used to receive a rotating linkage, such as a linkage used to provide high speed rotation of an array of ultrasound transducers mounted near the distal end of the linkage. Each device included in a lumen of the flexible shafts may be removable or configured to prevent removal.

The ablation catheter and esophageal probe of the present invention may include one or more functional elements, such as one or more location elements, sensors, transducers, antennas, or other functional components. Functional elements can be used to deliver energy such as electrodes delivering energy for tissue ablation, cardiac pacing or cardiac defibrillation. Functional elements can be used to sense a parameter such as tissue temperature; cardiac signals or other physiologic parameters; contact with a surface such as the esophageal or atrial walls of a patient; an energy parameter transmitted from another functional element such as amplitude, frequency; phase; direction; or wavelength parameters; and other parameters. In a preferred embodiment of the present invention, either or both the esophageal probe and the ablation catheter include multiple functional elements. In another preferred embodiment, either or both the ablation catheter and the esophageal probe include a deflectable distal end; such as a deflected end that causes one or more functional elements to make contact with tissue. Deflection means may include one or more of: a pull wire; an expandable cage such as an eccentric cage; an expandable balloon such as an eccentric balloon; an expandable cuff; a deflecting arm such as an arm which exits the flexible catheter shaft in a lateral direction; and a suction port.

The ablation catheter and esophageal probe of the present invention preferably include a handle on their proximal end. The handle may be attached to an outer sheath, allowing one or more inner shafts or tubes to be controlled with controls integral to the handle such as sliding and rotating knobs that are operable attached to those shafts or tubes. Alternatively, the handle may be attached to a shaft that is slidingly received by an outer sheath, such that an operator can advance and retract the shaft by advancing and retracting the handle and holding the sheath in a relatively fixed position. The handle may include one or more attachment ports, such as attachment ports which electrically connect to one or more wires; ports which provide connection to optical fibers; ports which fluidly connect to one or more conduits such as an endoflator for expanding a balloon with saline or a source of cooling fluids; and combinations thereof. Other controls may be integrated into the handle such as deflecting tip controls, buttons that complete a circuit or otherwise initiate an event such as the start of energy delivery to an ablation element. In addition, the handle may include other functional components including but not limited to: transducers such as a sound transducer which is activated to alert an operator of a change is status; a visual alert component such as an LED, a power supply such as a battery; a lock which prevents inadvertent activation of an event such as energy delivery; input and output devices that send and receive signals from the interface unit of the present invention; and combinations thereof.

The esophageal probe is for placing in the esophagus of a patient and comprises a flexible shaft with a location element. The esophageal probe includes one or more components and configurations as described hereabove. In a preferred embodiment, the esophageal probe provides a stethoscope function providing a signal proportional to the cardiac pulse waveform. The probe preferably includes an integral microphone that provides a signal representative of the cardiac pulse waveform. In another preferred embodiment, the esophageal probe includes an electrode on the outer wall near its distal end, the electrode sized and configured to deliver large amounts of electrical energy, in cooperation with another large electrode internal to or on the skin of the patient, to cause cardiac pacing or cardiac fibrillation.

The interface unit of the present invention provides energy to the ablation elements of the ablation catheter. In preferred embodiments, one or more ablation elements are electrodes configured to deliver RF energy. Other forms of energy, alternative or in addition to RF, may be delivered, including but not limited to: acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof. The ablation elements can deliver energy individually, in combination with or in serial fashion with other ablation elements. The ablation elements can be electrically connected in parallel, in series, individually, or combinations thereof. The ablation catheter may include cooling means to prevent undesired tissue damage and/or blood clotting. The ablation elements may be constructed of various materials, such as plates of metal and coils of wire for RF or other electromagnetic energy delivery. The electrodes can take on various shapes including shapes used to focus energy such as a horn shape to focus sound energy, and shapes to assist in cooling such as a geometry providing large surface area. Electrodes can vary within a single carrier assembly, such as a spiral array of electrodes or an umbrella tip configuration wherein electrodes farthest from the central axis of the catheter have the largest major axis. Wires and other flexible conduits are attached to the ablation elements, such as electrical energy carrying wires for RF electrodes or ultrasound crystals, and tubes for cryogenic delivery.

The ablation elements requiring electrical energy to ablate require wired connections to an electrical energy power source such as an RF power source. In configurations with large numbers of electrodes, individual pairs of wires for each electrode may be bulky and compromise the cross-sectional profile of the ablation catheter. In an alternative embodiment, one or more electrodes are connected in serial fashion such that a reduced number of wires, such as two wires, can be attached to two or more electrodes and switching or multiplexing circuitry are included to individually connect one or more electrodes to the ablative energy source. Switching means may be a thermal switch, such that as a first electrodes heats up, a single pole double throw switch change state disconnecting power from that electrode and attaching power to the next electrode in the serial connection. This integral temperature switch may have a first temperature to disconnect the electrode, and a second temperature to reconnect the electrode wherein the second temperature is lower than the first temperature, such as a second temperature below body temperature. In an alternative embodiment, each electrode is constructed of materials in their conductive path such that as when the temperature increased and reached a predetermined threshold, the resistance abruptly decreased to near zero, such that power dissipation, or heat, generated by the electrode was also near zero, and more power could be delivered to the next electrode incorporating the above switching means.

The interface unit of the present invention includes a user interface including components including but not limited to: an ultrasound monitor such as an ultrasound monitor in communication with one or more ultrasound crystals near a temperature sensor of the esophageal probe or ultrasound crystals within an electrode carrier assembly of the ablation catheter; an x-ray monitor such as a fluoroscope monitor used to measure the distance between two or more location elements; other user output components such as lights and audio transducers; input components such as touch screens, buttons and knobs; and combinations thereof. In a preferred embodiment, the interface unit provides functions in addition to providing the energy to the ablation catheter including but not limited to: providing a cardiac mapping function; providing cardiac defibrillation energy and control; providing cardiac pacing energy and control; providing a system diagnostic such as a diagnostic confirming proper device connection; providing the calculating function of the present invention; providing a signal processing function such as interpreting signals received from one or more sensors of the esophageal probe and/or the ablation catheter; providing drive signals and/or energy to one or more functional elements of the esophageal probe and/or the ablation catheter; providing a second energy type to the ablation elements of the ablation catheter; and combinations thereof.

In a preferred embodiment, the interface unit provides an analysis function to determine one or more system parameters that correlate to ablation settings, the parameters including but not limited to: an energy delivery amount; an energy delivery frequency; an energy delivery voltage; an energy delivery current; an *energy delivery temperature; an energy delivery rate; an energy delivery duration; an energy delivery modulation parameter; an energy threshold; another energy delivery parameter; a temperature threshold; an alarm threshold; another alarm parameter; and combinations thereof. The analysis function utilizes the calculated distance of the present invention to determine one or more system parameters such as a temperature threshold not to be exceeded within the esophagus of the patient. In a preferred embodiment, the interface unit receives temperature information from multiple sensors of the esophageal probe, and the highest reading received is compared to a temperature threshold, such as a temperature threshold dependant upon the distance between a location element of the esophageal probe and a location element of the ablation catheter. The analysis function includes one or more algorithms that mathematically process information such as signals received from sensors of the ablation catheter or esophageal probe; information entered into the user interface of the interface unit by the operator; embedded electronic information uploaded from the ablation catheter or esophageal probe such as information determined during the manufacture of the catheter or probe; and combinations thereof. In a preferred embodiment, the ablation setting determined by the analysis function is provided to the operator via a display or other user interface output component.

The location elements of the present invention can be configured in various forms including but not limited to: ultrasound transducers; radiographic markers; antennas; transducers such as sound or light transducers; magnets; and combinations thereof. In a preferred embodiment, a location element is in close proximity to a temperature sensor of the esophageal probe. In another preferred embodiment, a location element is in close proximity to an electrode of the ablation catheter. In another preferred embodiment, a location element is configured to also function as one or more of: an ablation element such as an RF electrode; a sensor such as a thermocouple. A location element may be secured to a portion of the ablation catheter or esophageal probe and/or a location element may be secured to a tubular device which is inserted into a lumen, such as a blind lumen, of the ablation catheter or esophageal probe.

The calculating means of the present invention, preferably at least in part integral to the user interface, performs one or more mathematical functions, signal processing functions; signal transmission functions; and combinations thereof to determine the distance between a location element of the esophageal probe and a location element of the ablation catheter. The calculating means of the present invention may include a function performed by a user of the system such as a distance value that is entered into the interface unit after a measurement is performed such as a measurement made from an IVUS monitor or a fluoroscopy screen. Parameters set by an operator via the user interface may be limited by the distance value determined by the calculating means. In a preferred embodiment, a maximum energy setting is limited by the determined distance. In another preferred embodiment, multiple distances between multiple location elements are determined by the calculating means. In another preferred embodiment, a refined distance more accurately representing the distance between a temperature sensor on the esophageal probe and an ablation element of the ablation catheter is determined by the calculating means.

In a preferred embodiment, when a temperature reaches a threshold that has been set utilizing the distance determined by the calculating means, one or more system parameters are modified. These modifications include but are not limited to: a threshold parameter such as an increased temperature threshold; an alarm or alert parameter such as an audible alarm "on" state; an energy parameter such as a parameter changing energy type or modifying energy delivery such as switching from RF energy to cryogenic energy or stopping energy delivery; a sensor parameter such as a parameter which activates one or more additional sensors; cooling apparatus parameter such as a parameter activating a cooling apparatus; a parameter that changes the polarity of energy delivery or the modulation of energy delivery such as a parameter that switches from monopolar to bipolar delivery or phased monopolar-bipolar to bipolar; and combinations thereof.

The system of the present invention preferably includes multiple functional elements integral to the ablation catheter and/or the esophageal probe. These functional elements may be mounted on the outer wall of the flexible shaft of the device. Alternatively or additionally, one or more functional elements may be mounted to a balloon, such as a perfusion balloon, eccentric balloon or concentric balloon and/or elements may be mounted to a carrier assembly such as a carrier assembly than exits the distal end or a side hole of the flexible shaft. These functional elements may be covered with a membrane and multiple elements may be configured in an array such as an array that is rotated within a lumen of the flexible shaft. Functional elements may be placed on the patient's chest, such as EKG electrodes, pacing electrodes or defibrillation electrodes. Functional elements include but are not limited to: sensors such as temperature sensors; transmitters such as energy transmitting electrodes, antennas and electromagnetic transmitters; imaging transducers; signal transmitters such as drive signal transmitters. Electrodes may include one or more of: a metal such as gold, platinum; steel; copper and aluminum; a metal coating; a metal plating; a conductive polymer; a conductive paint or coating; and combinations thereof. Electrodes may be plates or coils, may take the form of a dome-like protuberance, and a transmitting electrode may also function as a sensor such as an ultrasound transducer that transmits and receives ultrasound signals to create a cross-sectional image.

Functional elements may include sensing functions such a sensor to detect physiologic parameter. In a preferred embodiment, one or more functional elements are configured as sensors to receive signals that are indicative of one or more cardiac functions of the patient. Sensors may include but are not limited to: an electrical signal sensor such as a cardiac electrode; a temperature sensor such as a thermocouple; an imaging transducer such as an array of ultrasound crystals; a pressure sensor; a pH sensor; a blood sensor, a respiratory sensor; an EEG sensor, a pulse oximetry sensor; a blood glucose sensor; an impedance sensor; a contact sensor; a strain gauge; an acoustic sensor such as a microphone; a photodetector such as an infrared photodetector; and combinations thereof. Functional elements alternatively or additionally include one or more transducers. The transducer may be a location element; a transmitter such as a transmitting antenna, an RF electrode, a sound transmitter; a photodiode, a pacing electrode, a defibrillation electrode, a visible or infrared light emitting diode and a laser diode; a visualization transducer such as an ultrasound crystal; and combinations thereof.

Numerous kit configurations are also to be considered within the scope of this application. An ablation catheter is provided with multiple carrier assemblies. These carrier assemblies can be removed for the tubular body member of the catheter, or may include multiple tubular body members in the kit. The multiple carrier assemblies can have different patterns, different types or amounts of electrodes, and have numerous other configurations including compatibility with different forms of energy. Multiple sensors, such as EKG skin electrodes may be included, such as electrodes that attach to the interface unit of the present invention. A kit may include one or more catheters, such as an ultrasound catheter, which are configured to enter and extend distally in a lumen of the ablation catheter and/or the esophageal probe. One or more esophageal probes may be included such as probes with different tip or sensor configurations.

Though the ablation device has been described in terms of its preferred endocardial and transcutaneous method of use, the array may be used on the heart during open-heart surgery, open-chest surgery, or minimally invasive thoracic surgery. Thus, during open-chest surgery, a short catheter or cannula carrying the carrier assembly and its electrodes may be inserted into the heart, such as through the left atrial appendage or an incision in the atrium wall, to apply the electrodes to the tissue to be ablated. Also, the carrier assembly and its electrodes may be applied to the epicardial surface of the atrium or other areas of the heart to detect and/or ablate arrhythmogenic foci from outside the heart.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:
1. A tissue ablation system comprising:
  an esophageal probe having a flexible shaft with a proximal end, a distal end, an exterior wall, and a first location element;
  a first catheter including at least one ablation element for delivering energy to cardiac tissue, the first catheter having a flexible shaft with a proximal end, a distal end, an exterior wall, and a second location element; and
  an interface unit for delivering energy to the first catheter, the interface unit programmed to:
    calculate a distance between the first and second location elements; and
    determine a temperature threshold for the ablation element based at least in part on the calculated distance.
2. The system of claim 1 wherein a parameter of said system is modified when a sensed temperature reaches the temperature threshold.
3. The system of claim 2 wherein the parameter of said system is selected from the group consisting of a threshold parameter, an alarm parameter, an energy parameter, a sensor parameter, a cooling apparatus parameter, and combinations thereof.
4. The system of claim 2 wherein the parameter of said system is the energy delivered.
5. The system of claim 4 wherein the parameter of said system is modified in a manner selected from the group consisting of changing the type or types of energy delivered, changing the intensity of energy delivered, changing the frequency of energy delivered, changing a pulse width modulation parameter of energy delivered, and combinations thereof.
6. The system of claim 4 wherein the energy delivered comprises RF energy.
7. The system of claim 4 wherein the energy delivered comprises thermal energy.
8. The system of claim 7 wherein the energy delivered is modified by changing from monopolar to bipolar delivery.
9. The system of claim 8 wherein the temperature threshold is also modified.
10. The system of claim 7 wherein the energy delivered is modified by changing from bipolar to monopolar delivery.
11. The system of claim 7 wherein the energy delivered is modified by changing from a phased monopolar-bipolar to bipolar delivery.
12. The system of claim 1 wherein either the first location element or the second location element comprises a transmitting antenna.
13. The system of claim 12 wherein the other location element comprises a receiving antenna.
14. The system of claim 12 wherein the other location element also comprises a transmitting antenna.
15. The system of claim 1 wherein either the first location element or the second location element comprises a transmitter selected from the group consisting of a sound transmitter, an ultrasound transmitter and combinations thereof.
16. The system of claim 15 wherein the transmitter is capable of creating a cross-sectional image of the neighboring tissue.
17. The system of claim 1 further comprising a functional element integrated into one or more of the first and second ablation catheters.
18. The system of claim 17 wherein the functional element comprises a sensor.
19. The system of claim 18 wherein the sensor is selected from the group consisting of an electrical signal sensor, an imaging transducer, a pressure sensor, a pH sensor, a physiologic sensor, a respiratory sensor, an EEG sensor, a pulse oximetry sensor, a blood glucose sensor, an impedance sensor, a contact sensor, a strain gauge an acoustic sensor, and combinations thereof.
20. The system of claim 18 wherein the sensor is capable of receiving signals indicative of the status of one or more cardiac functions.
21. The system of claim 20 wherein the signals indicative of the status of one or more cardiac functions comprise electrical signals.
22. The system of claim 17 wherein the functional element comprises a sensor capable of mapping conductive pathways of the heart.
23. The system of claim 22 wherein the sensor includes at least one electrode.
24. The system of claim 23 wherein the at least one electrode is capable of delivering energy to tissue.
25. The system of claim 17 wherein the functional element comprises an acoustic sensor.
26. The system of claim 25 wherein the acoustic sensor provides a signal proportional to a cardiac pulse waveform.

27. The system of claim 17 wherein the functional element comprises a transmitter capable of emitting electrical energy and/or electrical signals.

28. The system of claim 27 wherein the transmitter comprises a pacing electrode.

29. The system of claim 27 wherein the transmitter comprises a defibrillation electrode having at least one contact.

30. The system of claim 29 further comprising an external electrode, said electrode in electrical communication with a patient's skin.

31. The system of claim 30 wherein the esophageal probe is positioned such that the defibrillation electrode of the esophageal probe is in contact with a lower third of a patient's esophageal wall.

32. The system of claim 30 further comprising a defibrillation generator for generating electrical pulses transmitted through the esophageal wall to defibrillate a patient's heart, a first electrical conductor connecting the defibrillation electrode of the esophageal probe to said defibrillation generator and a second electrical conductor connecting the external electrode to said defibrillation generator.

33. The system of claim 17 wherein the functional element comprises an electrode.

34. The system of claim 33 wherein the electrode is selected from the group consisting of a plate and a coil.

35. The system of claim 33 wherein the electrode comprises a sensor and a transmitter.

36. The system of claim 1 wherein the energy is selected front the group consisting of sound energy, electromagnetic energy, thermal energy, chemical energy, light energy, mechanical energy, radiation and combinations thereof.

37. The system of claim 1 wherein the interface unit is capable of adjusting an ablation parameter selected from the group consisting of, a energy delivery amount, an energy delivery frequency, an energy delivery voltage, an energy delivery current, an energy delivery temperature, an energy delivery rate, an energy delivery duration, an energy delivery modulation parameter, an energy threshold, an ablation temperature and combinations thereof.

38. The system of claim 37 wherein the ablation parameter comprises an ablation temperature.

39. The system of claim 38 wherein the ablation temperature is adjusted when it reaches the threshold temperature.

40. The system of claim 1 wherein the interface unit includes a user interface, said user interface providing means for adjusting one or more ablation parameters of said system.

41. The system of claim 40 wherein a range of settable values for the one or more ablation settings is modified based on an observed distance between the first location element and the second location element.

42. An ablation system comprising:
a first catheter having at least one ablation element for delivering energy to cardiac tissue;
a second catheter having a sensor and a location element; and
an interface unit for providing energy to the at least one ablation element, the interface unit operable to determine the distance between the location element and the at least one ablation element, and define a temperature threshold for the ablation element based at least in part on the determined distance.

\* \* \* \* \*